US010400944B2

(12) United States Patent
Bax et al.

(10) Patent No.: US 10,400,944 B2
(45) Date of Patent: Sep. 3, 2019

(54) COUNTERBALANCE SYSTEM AND/OR A METHOD FOR COUNTERBALANCING A LOAD

(71) Applicants: CENTRE FOR IMAGING TECHNOLOGY COMMERCIALIZATION, London (CA); THE UNIVERSITY OF WESTERN ONTARIO, London (CA)

(72) Inventors: Jeffrey Bax, London (CA); Christopher Waring, London (CA); Aaron Fenster, London (CA)

(73) Assignees: Centre for Imaging Technology Commercialization, London, Ontario (CA); The University of Western Ontario, London, Ontario (CA)

( * ) Notice: Subject to any disclaimer, the term of this patent is extended or adjusted under 35 U.S.C. 154(b) by 41 days.

(21) Appl. No.: 15/562,976

(22) PCT Filed: Mar. 31, 2015

(86) PCT No.: PCT/CA2015/000203
§ 371 (c)(1),
(2) Date: Sep. 29, 2017

(87) PCT Pub. No.: WO2016/154708
PCT Pub. Date: Oct. 6, 2016

(65) Prior Publication Data
US 2018/0112817 A1    Apr. 26, 2018

(51) Int. Cl.
*F16M 11/04*    (2006.01)
*F16M 13/00*    (2006.01)
(Continued)

(52) U.S. Cl.
CPC ......... *F16M 13/005* (2013.01); *A61B 8/4218* (2013.01); *A61B 8/4245* (2013.01);
(Continued)

(58) Field of Classification Search
USPC ...................................... 248/123.11
See application file for complete search history.

(56) References Cited

U.S. PATENT DOCUMENTS 4,160,536 A * 7/1979 Krogsrud ............... F16M 11/04
                                                           248/123.11
4,883,249 A * 11/1989 Garland ............... B25J 19/0016
                                                           248/566
(Continued)

*Primary Examiner* — Monica E Millner
(74) *Attorney, Agent, or Firm* — Fasken Martineau DuMoulin LLP; Mark D. Penner

(57) ABSTRACT

Disclosed is a counterbalance system for moving a payload and a method for counterbalancing the payload. The system and method comprise a resilient member that is in communication with the payload to be moved and two resilient members that are in communication with either end of the first resilient member. An actuator is in communication with the first and third resilient members and a payload arm, attached to the payload, is in communication with the first and second resilient members. The resilient members may be compressed and relaxed during movement of the actuator and the payload arm so that energy may be transferred between the system and the payload to counterbalance the weight of the payload.

20 Claims, 23 Drawing Sheets

(51) Int. Cl.
  *F16M 11/12* (2006.01)
  *B65G 9/00* (2006.01)
  *A61B 8/00* (2006.01)

(52) U.S. Cl.
  CPC ............. *B65G 9/00* (2013.01); *F16M 11/046* (2013.01); *F16M 11/048* (2013.01); *F16M 11/12* (2013.01); *A61B 8/44* (2013.01); *F16M 2200/041* (2013.01); *F16M 2200/063* (2013.01)

(56) References Cited

U.S. PATENT DOCUMENTS

| | | | | |
|---|---|---|---|---|
| 5,435,515 A * | 7/1995 | DiGiulio | ................ | F16M 11/10 224/908 |
| 5,609,316 A * | 3/1997 | Tigliev | .................. | A61B 90/25 248/123.11 |
| 7,562,851 B2 * | 7/2009 | Hein | .................. | F16M 11/2014 248/276.1 |
| 7,618,016 B2 * | 11/2009 | Brown | ..................... | F16F 1/12 224/185 |
| 7,837,674 B2 * | 11/2010 | Cooper | ................ | B25J 19/0016 606/1 |
| 8,899,125 B2 * | 12/2014 | Bax | ...................... | B25J 19/0016 16/289 |
| 2005/0193451 A1 * | 9/2005 | Quistgaard | .......... | A61B 5/6843 414/1 |
| 2007/0080275 A1 * | 4/2007 | Stachowski | .............. | A61B 8/00 248/323 |
| 2014/0121675 A1 * | 5/2014 | Bax | .................... | A61B 17/3403 606/130 |
| 2014/0135790 A1 * | 5/2014 | Fenster | ................. | A61B 90/11 606/130 |
| 2015/0168179 A1 * | 6/2015 | Bax | ....................... | G01B 5/004 324/207.25 |
| 2015/0265048 A1 * | 9/2015 | Lindblad | ............ | A47B 81/062 248/123.11 |

* cited by examiner

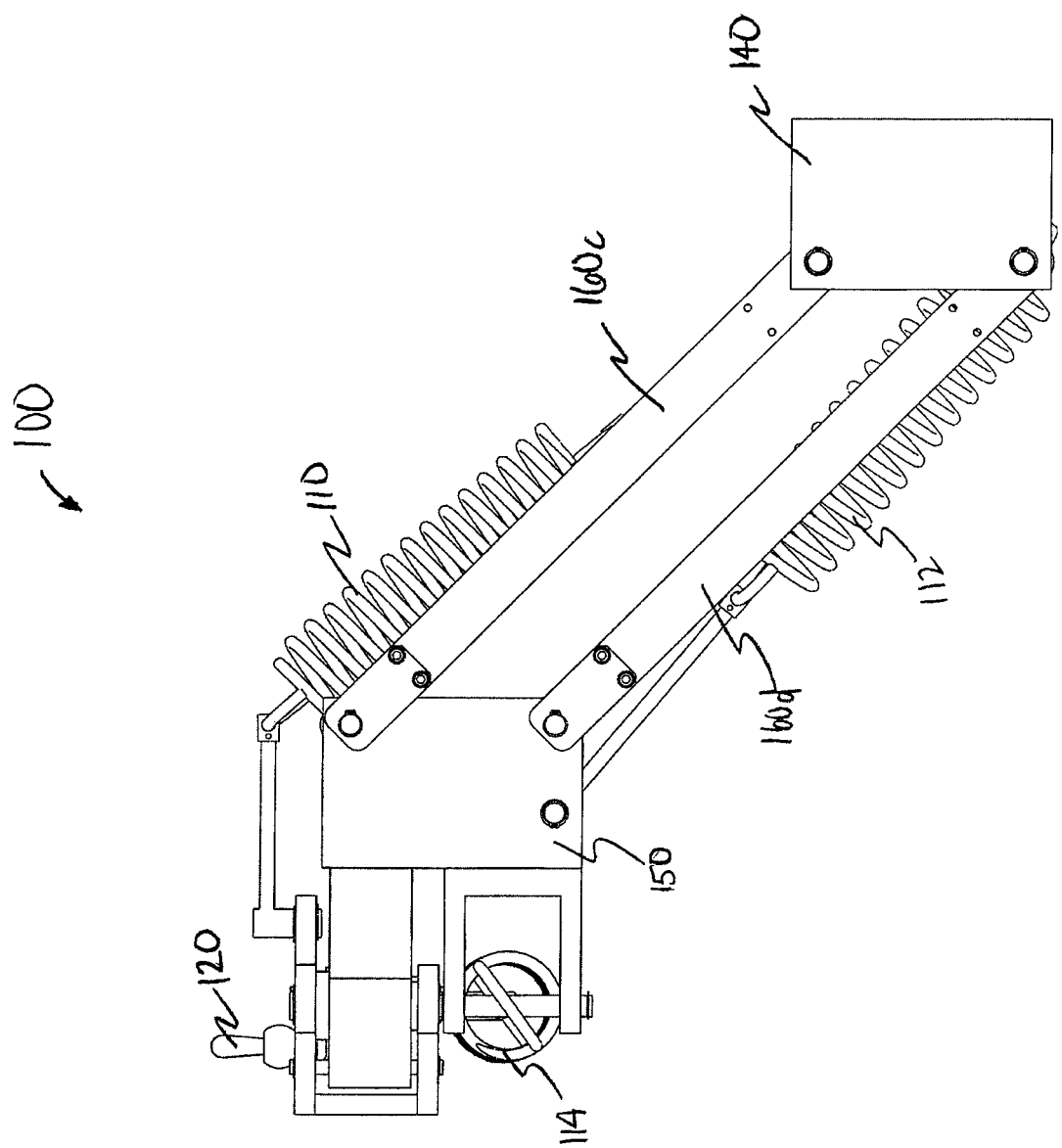

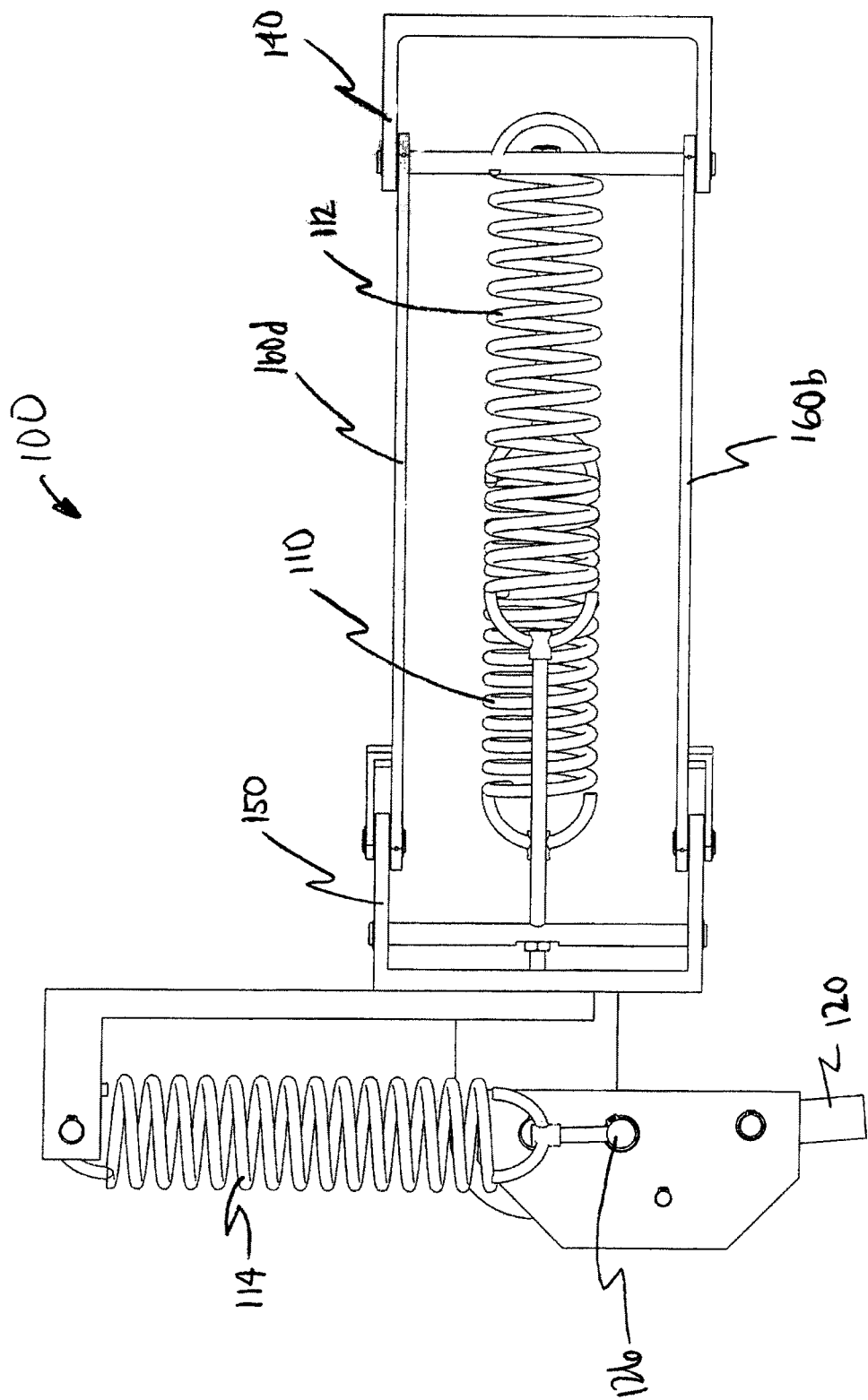

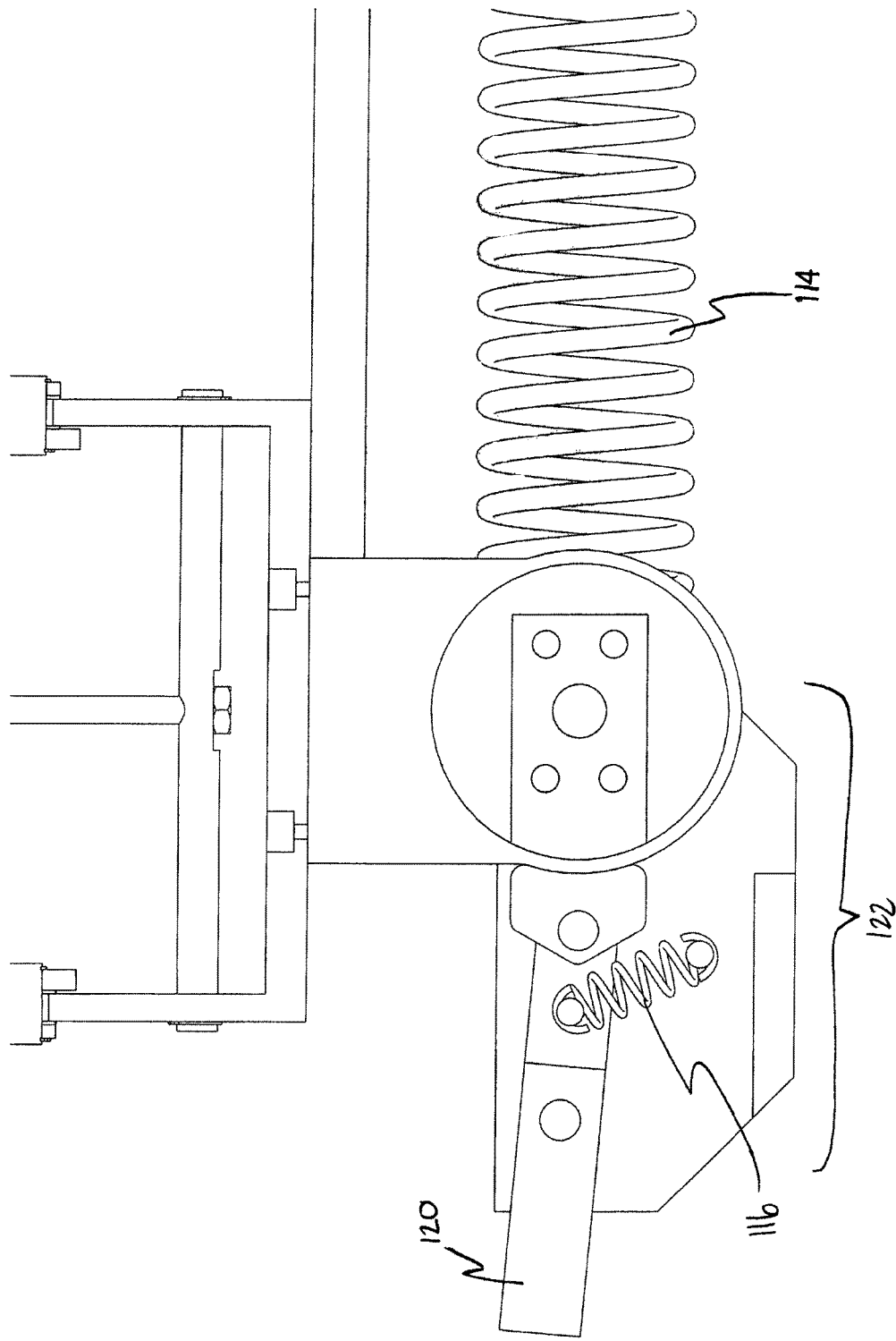

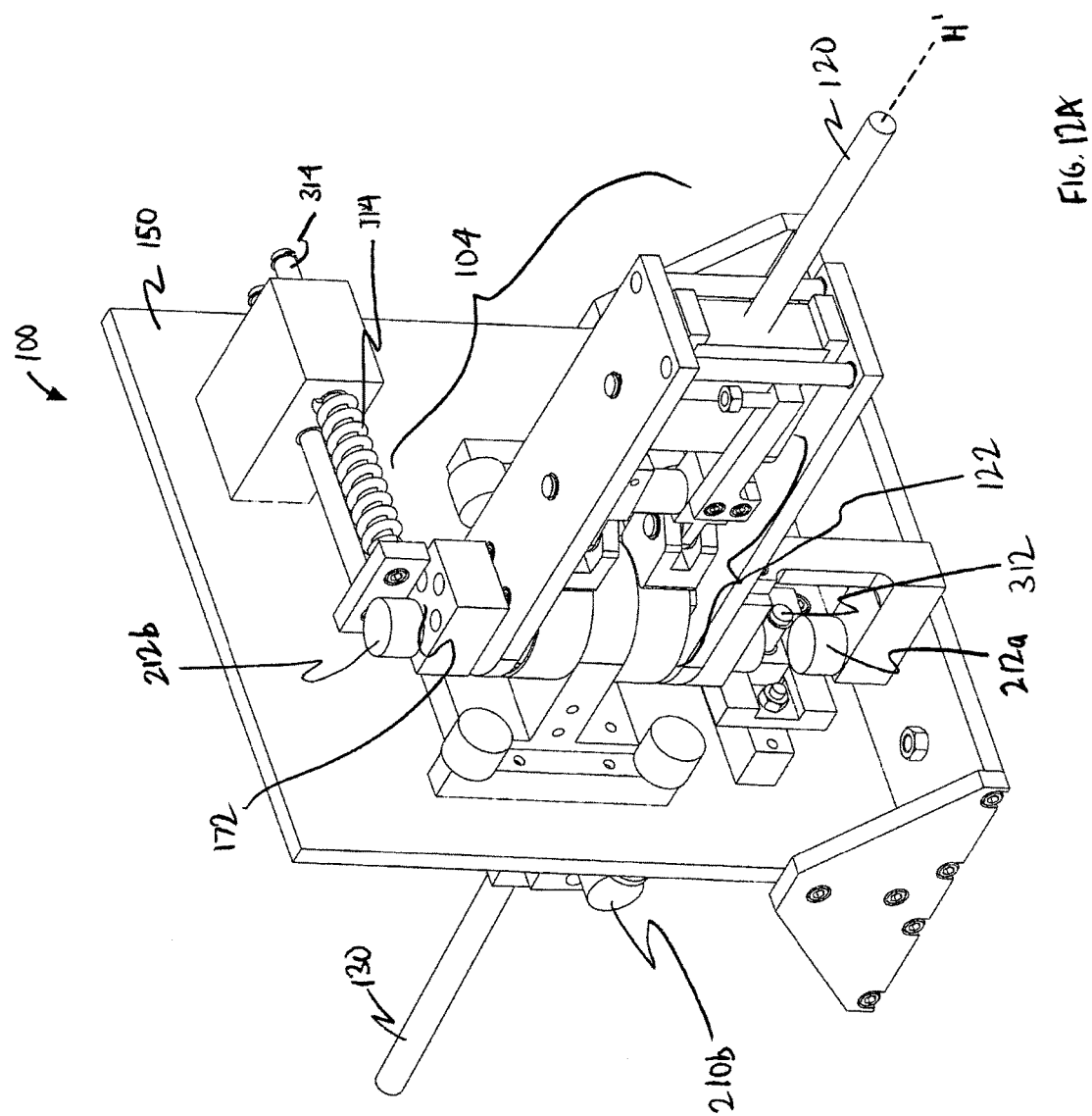

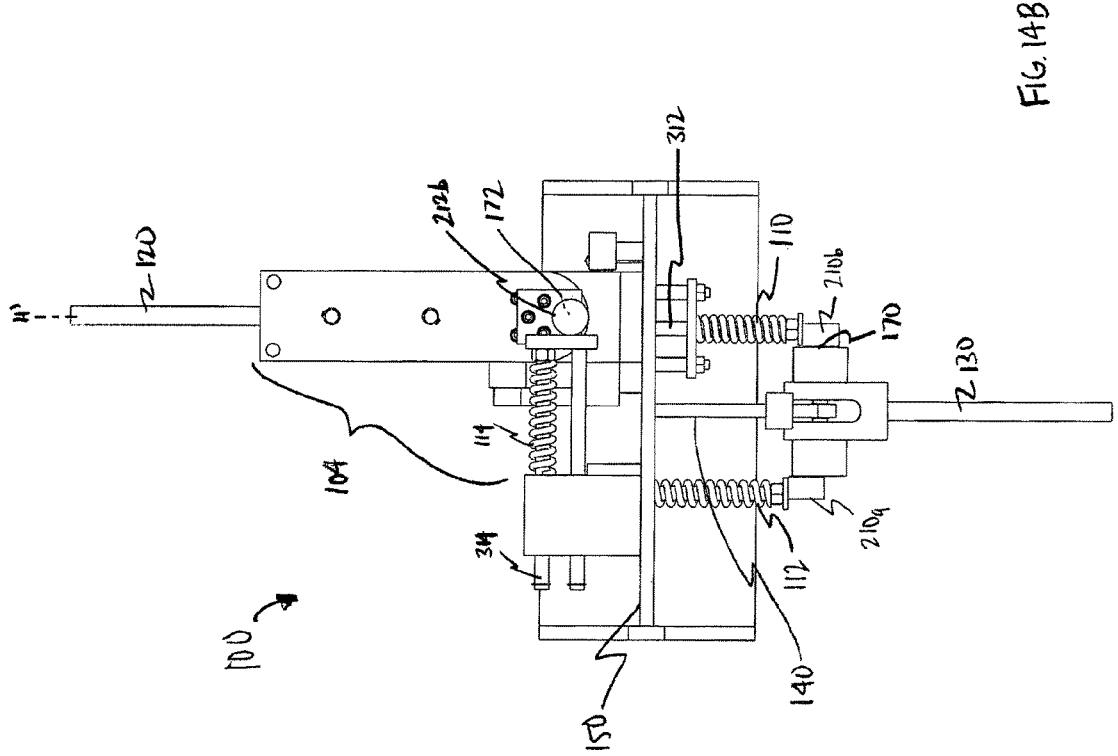

COUNTERBALANCE SYSTEM AND/OR A METHOD FOR COUNTERBALANCING A LOAD

CROSS-REFERENCE TO RELATED APPLICATIONS:

This application is a § 371 national phase of International Application No. PCT/CA2015/000203, filed on Mar. 31, 2015, which application is incorporated by reference herein.

FIELD OF THE INVENTION

The present invention relates to a counterbalancing system, and more particularly to a multiple resilient member system for counterbalancing a payload.

BACKGROUND OF THE INVENTION

Many scientific, medical and industrial tasks involve the deployment of objects or instruments, which may need to be held aloft and manipulated in space for extended periods of time, resulting in repetitive stress to the user. The resulting repetitive stresses are known to be a cause of work-related trauma.

For example, work-related musculoskeletal disorders have been identified as a widespread problem amongst diagnostic medical sonographers and vascular technologists. In 2006, approximately 46,000 sonographer and vascular technologist job positions existed in the United States. A representative survey reported nearly 90% of sonographers and vascular technologists complete ultrasound scans while in some form of pain. Aggravating factors for pain during procedures was reported by sonographers to include sustained and repeated twisting of the neck and body, sustained arm abduction and application of pressure on the ultrasound transducer.

In a further example, poor ergonomics within industrial settings may also adversely affect the productivity and the health and safety of workers. Heavy tools or parts may require maneuvering in repetitive or awkward motions by workers within industrial settings. Workers may also be required to maintain fixed poses for extended periods of time. To improve worker ergonomics, devices have been developed to counterbalance tools or parts. These devices counteract the force of gravity to simulate the tool floating in air and improve worker ergonomics.

In the field of diagnostic medical sonography and vascular technology, for example, previous counterbalancing arms may have used high torque motors to counterbalance the load weight creating potential harm for a patient. In the event of a malfunction, the motors may potentially drive the arm into the patient with a minimum force of twice the weight of the arm. In the event of a power failure, a traditional arm may lose its pose and slump under its own weight as the motors can no longer counterbalance the weight. While brakes may have been applied to prevent traditional arms from slumping in a power failure, the traditional arm may become fully locked (i.e., un-adjustable) until power is restored.

Prior attempts, if any, to solve problems associated with prior art devices and/or methods may have been unsuccessful and/or had one or more disadvantages associated with them. Prior art devices and/or methods have been ill-suited to solve the stated problems and/or the shortcomings which have been associated with them.

Various prior art counterbalance systems have attempted to reduce the many aggravating factors reported by workers in the above-noted fields, including United States Patent Application No. 2010/0319164 for Counterbalance Assembly to Bax et al. (discloses a spring counterbalance system only for a single rigid arm or link) and Bax, Jeffrey et al., in Med. Phys., vol 35, no. 12, pp 5397-5410, 2008 entitled Mechanically Assisted 3D Ultrasound Guided Prostate Biopsy System.

In addition, there may be a number of known articulating arms that are configured to support a device of varying masses, but most have significant drawbacks. Some of these known arms may use a coiled spring having a fixed uniform spring rate as described in U.S. Pat. No. 8,066,251. In these arms, when the mass is varied, the coiled spring assembly disadvantageously may not be adjustable and a swap may need to be made between devices as well changing the internal component of an articulating arm (i.e., the spring). Many of these arms may also use a spring-cable-pulley system; particularly with arms consisting of a series of interconnecting links as the type that may be described in U.S. Pat. Nos. 5,435,515, 7,618,016, and 7,837,674. Previously, it may also have been known to use torsion springs in joints of the arm to generate torque forces which counter the torque loads in the joints of the arm. Furthermore, the concept of using a combination of springs and weights to counterbalance a payload may have been known as described in published U.S. Application No. 2005/0193451. A link assembly for a robot arm or snake arm consisting of two or more link members/segments in series that can be manipulated to flow axially along its length to guide a segment end to a given location may be known as described in U.S. Pat. No. 7,543,518. Also, a counterbalanced set-up arm to support a robot arm comprised of multiple joint arms, including a linkage and spring-cable-pulley balancing mechanism may also have been known as taught by U.S. Pat. No. 7,837,674.

Accordingly, there is a need for an improved counterbalancing assembly for an arm. What is needed is a counterbalance apparatus and/or method that overcomes one or more of the limitations associated with the prior art. It may be advantageous to provide an apparatus and/or method which allow the user to quickly pick up a payload with minimal effort.

It is an object of the present invention to obviate or mitigate one or more of the aforementioned disadvantages and/or shortcomings associated with the prior art, to provide one of the aforementioned needs or advantages, and/or to achieve one or more of the aforementioned objectives of the invention.

SUMMARY OF THE INVENTION

According to an aspect of one preferred embodiment of the invention, there is disclosed a counterbalance system for engaging a payload having a load vector in the direction of gravity is provided. The system includes a payload (K1) member, a payload compensation (K2) member, an actuator compensation (K3) member, an actuator and a payload arm. The payload (K1) member is in communication with the payload to be engaged. The payload compensation (K2) member and the actuator compensation (K3) member are in communication with either end of the payload (K1) member. The actuator, having a loaded and an unloaded position, is in communication with the payload (K1) and the actuator compensation (K3) members, the payload (K1) and the actuator compensation (K3) members may be adapted to transfer an actuator energy during movement of the actuator between the loaded and unloaded positions. The payload arm may be adapted to support the payload, having a load-bearing and a neutral position, in communication with the payload (K1) and the payload compensation (K2) members, the payload (K1) and the payload compensation (K2) members may be adapted to transfer a support energy during movement of the payload arm between the load-bearing and neutral positions. Movement of the actuator to the loaded position when the payload arm is in the neutral position, transfers the actuator energy and the support energy to generate a lift vector at the payload to counterbalance the load vector.

According to an aspect of one preferred embodiment of the invention, the payload arm may preferably, but need not necessarily, rotate about a first pivot and the actuator arm rotates about a second pivot.

According to an aspect of one preferred embodiment of the invention, the payload (K1) member, the payload compensation (K2) member and the actuator compensation (K3) member may preferably, but need not necessarily, be adapted to exert an expansion force.

According to an aspect of one preferred embodiment of the invention, the payload (K1) member, the payload compensation (K2) member and the actuator compensation (K3) member may preferably, but need not necessarily, be compression springs.

According to an aspect of one preferred embodiment of the invention, the system may preferably, but need not necessarily, comprise first and second cams adapted to transfer the support energy between the payload (K1) member and the payload compensation (K2) member and third and fourth cams to transfer the actuator energy between the payload (K1) member and the actuator compensation (K3) member.

According to an aspect of one preferred embodiment of the invention, the system may preferably, but need not necessarily, comprise first and second cams adapted to transfer the support energy between the payload (K1) member and the payload compensation (K2) member and third and fourth cams to transfer the actuator energy between the payload (K1) member and the actuator compensation (K3) member.

According to an aspect of one preferred embodiment of the invention, the first and second cams may preferably, but need not necessarily, be mounted eccentrically in relation to the first pivot and the third and fourth cams may preferably, but need not necessarily, be mounted eccentrically in relation to the second pivot.

According to an aspect of one preferred embodiment of the invention, the payload (K1) member, the payload compensation (K2) member and the actuator compensation (K3) member may preferably, but need not necessarily, be adapted to exert a compression force.

According to an aspect of one preferred embodiment of the invention, the payload (K1) member, the payload compensation (K2) member and the actuator compensation (K3) member are preferably, but need not necessarily, extension springs.

According to an aspect of one preferred embodiment of the invention, the payload (K1) member and the payload compensation (K2) member are preferably, but need not necessarily, attached eccentrically in relation to one another to facilitate transfer of the support energy and the payload (K1) member and the actuator compensation (K3) member are preferably, but need not necessarily, attached eccentrically in relation to one another to facilitate transfer of the actuator energy.

According to an aspect of one preferred embodiment of the invention, the system preferably, but need not necessarily, comprises a brake adapted to maintain the actuator at a position.

According to an aspect of one preferred embodiment of the invention, the position of the brake preferably, but need not necessarily, corresponds to with the load vector.

According to an aspect of one preferred embodiment of the invention, there is disclosed a method of engaging a payload having a load vector in the direction of gravity using a counterbalance system. The method includes step (a), (b), (c), and (d). In step (a), a payload (K1) member is positioned in communication with the payload to be engaged. In step (b), a payload compensation (K2) and an actuator compensation (K3) member are positioned in communication with either end of the payload (K1) member. In step (c), an actuator, moveable between a loaded and an unloaded position, is configured for communication with the payload (K1) and the actuator compensation (K3) members to transfer an actuator energy during movement of the actuator between the loaded and unloaded positions. In step (d), a payload arm adapted to support the payload, moveable between a load-bearing and a neutral position, is configured for communication with the payload (K1) and the actuator compensation (K2) members to transfer a support energy during movement of the payload arm between the load-bearing and neutral positions. Movement of the actuator to the loaded position when the payload arm is in the neutral position, transfers the actuator energy and the support energy to generate a lift vector at the payload to counterbalance the load vector.

According to an aspect of one preferred embodiment of the invention, in step (d), the payload arm preferably, but need not necessarily, rotates about a first pivot and the actuator arm rotates about a second pivot.

According to an aspect of one preferred embodiment of the invention, in steps (a) and (b), the payload (K1) member, the payload compensation (K2) member and the actuator compensation (K3) member are preferably, but need not necessarily, adapted to exert an extension force.

According to an aspect of one preferred embodiment of the invention, in steps (a) and (b), the payload (K1) member, the payload compensation (K2) member and the actuator compensation (K3) member are preferably, but need not necessarily, compression springs.

According to an aspect of one preferred embodiment of the invention, the method may preferably, but need not necessarily, further include the step of configuring first and second cams adapted to transfer the support energy between the payload (K1) member and the payload compensation (K2) member and third and fourth cams to transfer the actuator energy between the payload (K1) member and the actuator compensation (K3) member.

According to an aspect of one preferred embodiment of the invention, the step of configuring the cams may preferably, but need not necessarily, further include the step of mounting the first and second cams eccentrically in relation to the first pivot and the third and fourth cams eccentrically in relation to the second pivot.

According to an aspect of one preferred embodiment of the invention, in steps (a) and (b), the payload (K1) member, the payload compensation (K2) member and the actuator compensation (K3) member may preferably, but need not necessarily, be adapted to exert a compression force.

According to an aspect of one preferred embodiment of the invention, in steps (a) and (b), the payload (K1) member, the payload compensation (K2) member and the actuator compensation (K3) member may preferably, but need no necessarily, be extension springs.

According to an aspect of one preferred embodiment of the invention, the method may preferably, but need not necessarily, also include a step of attaching the payload (K1) member and the payload compensation (K2) member eccentrically in relation to one another to facilitate transfer of the support energy and the payload (K1) member and the actuator compensation (K3) member eccentrically in relation to one another to facilitate transfer of the actuator energy.

According to an aspect of one preferred embodiment of the invention, the method may preferably, but need not necessarily, also include a step of maintaining the actuator at a position using a brake.

According to an aspect of one preferred embodiment of the invention, the method may preferably, but need not necessarily, also include a step of configuring the position of the brake to correspond to the load vector.

Other advantages, features and characteristics of the present invention, as well as methods of operation and functions of the related elements of the apparatus and method, and the combination of steps, parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the apparatus and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings:

FIGS. 6A, 6B, and 6C are side views of the system of FIG. 5 with the lifting arm horizontal, raised, and lowered, respectively;

FIG. 9 is a bottom view of the system of FIG. 5;

FIG. 10 is an enlarged top view of the system of FIG. 6;

DETAILED DESCRIPTION OF THE PREFERRED EMBODIMENTS

Figure 1:
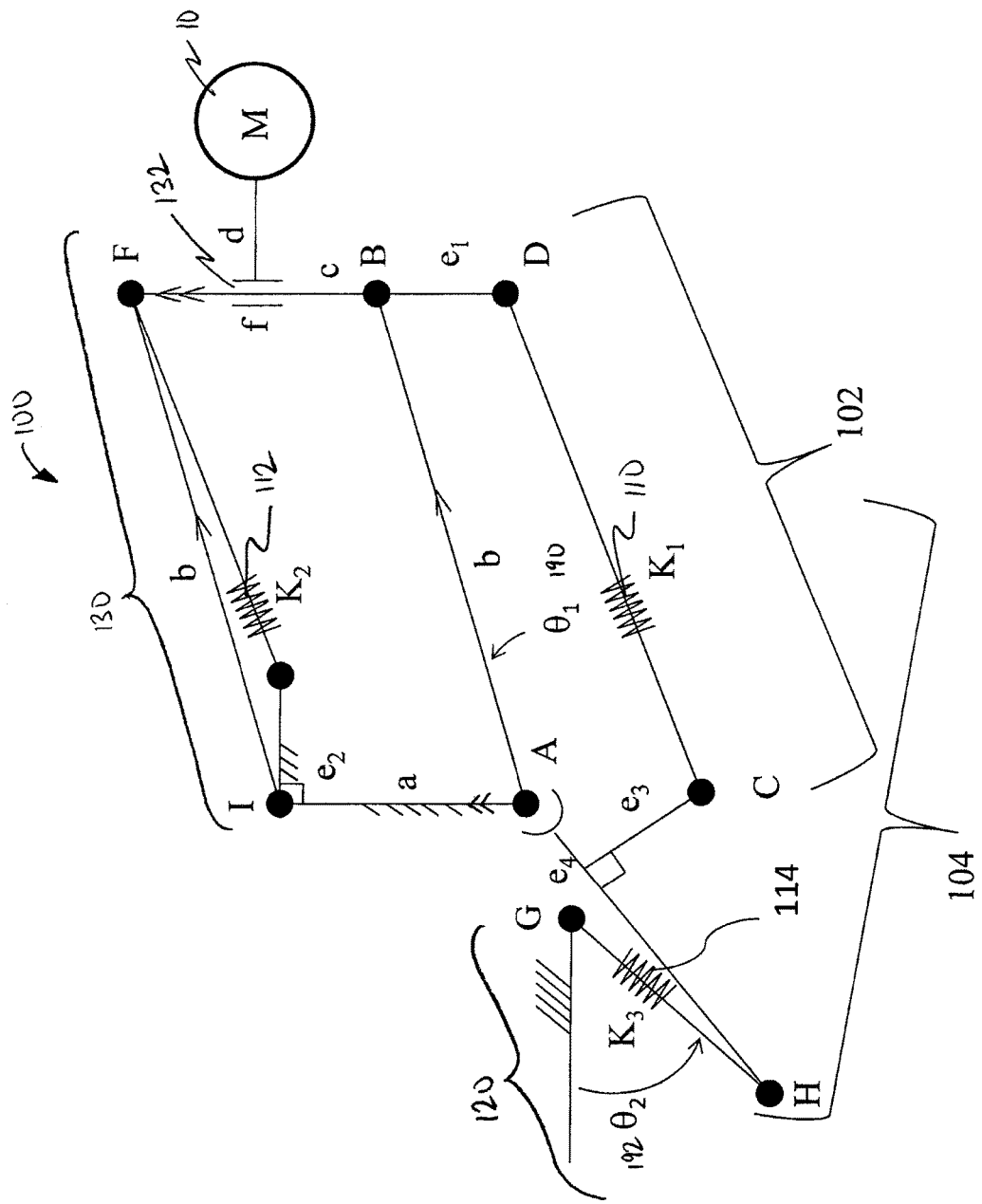
FIG. 1 is a schematic representation of a counterbalance system in a parallelogram arm configuration with a payload.

The description that follows, and the embodiments described therein, is provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated in order to more clearly depict certain embodiments and features of the invention.

In this disclosure, a number of terms and abbreviations are used. The following definitions of such terms and abbreviations are provided.

As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

In the description and drawings herein, and unless noted otherwise, the terms "vertical", "lateral" and "horizontal", are generally references to a Cartesian co-ordinate system in which the vertical direction generally extends in an "up and down" orientation from bottom to top (y-axis) while the lateral direction generally extends in a "left to right" or "side to side" orientation (x-axis). In addition, the horizontal direction extends in a "front to back" orientation and can extend in an orientation that may extend out from or into the page (z-axis). Unless indicated otherwise, the force or vector of gravity acts parallel to the y-axis (e.g., the vertical direction) in a general downward manner.

As used herein, a person skilled in the relevant art would understand that a parallelogram is a quadrilateral with two pairs of parallel sides. The opposite or facing sides of a parallelogram are of equal length and the opposite angles of a parallelogram are of equal measure. Parallelograms may include, but are not limited to, rhomboids, rectangles, rhombuses, and squares. Those skilled in the relevant art would understand that a parallelogram of the present invention may be disposed in single or compound linkages, wherein it will be understood that a compound parallelogram generally may comprise two parallelograms with a common side.

As used herein, a person skilled in the relevant art would understand that a "resilient member" may comprise one or more of any of the following elastic, pneumatic, gas spring, constant force spring motor, or other device adapted to store or exert mechanical energy, generate force and/or that is back-drivable (e.g., force applied to an output can move an input). In a preferred embodiment, a resilient member may comprise a spring-like device and in a more preferred embodiment, may comprise a compression or extension spring. While springs may preferably be represented in the figures of the present application, persons skilled in the art will understand that any force generating device may be used in the system described herein.

As used herein, a person skilled in the relevant art will understand a "spring-like device" to refer to any device or structure that acts substantially like a compression or tension spring in providing resistance to a linear compression, expansion and/or tension along a longitudinal axis or resistance to bending which may produce a force at right angles to a long axis of the spring (e.g., a leaf or torsion spring). An example of a spring-like device is a unit of rubber or other resilient material or a pneumatic pressurized cylinder any one of which may be used in an equivalent manner to a compression or tension spring by providing resistance to a linear force along a longitudinal axis. Another example of a spring-like device is a spring, such as a compression spring or a tension spring. Compression springs are an example of a low cost force generating device that may be utilized to provide a simplified arrangement within the counterbalance assembly. A compression spring includes a longitudinal axis along which linear compressive forces may be imposed as a result of rotational movement of a mechanical arm. Examples of compression springs include relatively standard die springs as commonly available in the industry. The exact number and size of such resilient members used in the counterbalance assembly described herein can vary depending upon the counterbalance torque desired, the size of the robotic arm involved, and the like, as will be recognized by the skilled person.

As used herein, a person skilled in the relevant art will be understood that a force generating device refers to any structure or device which provides resistance to forces (e.g. compressive, expansive or tensile forces) applied thereto or imposed thereon (e.g. linear deflection forces). It will be also understood that a force generating device may generate force. For example, it will be understood that any structure or device that exhibits resistance to linear compression or tension along an axis (e.g. a longitudinal axis) thereof may be useful as a force generating device. It will be further understood, therefore, that a force generating device may include a longitudinal axis along which linear forces may be imposed. As will be understood from the description of the present invention provided herein, a force generating device may, in a preferred embodiment, interact with a cam to convert rotational movement into linear deflection of the force generating device. An example of a force generating device is a spring-like device. The force generating device may be adjustable such that the resistive force provided by the force generating device may be increased or decreased to allow for variation in mechanical arms. A force generating device may interact with at least one other element or component of the present invention (e.g. a cam, etc.) in accordance with embodiments of the present invention.

As used herein, a person skilled in the relevant art will understand a "cam" to refer to component that rotates or reciprocates to provide a prescribed or variable motion in an interacting element, which is often termed the follower. Skilled readers may understand that the cam itself need not move and may be fixed in place as the component rotates about the cam. In the context of the counterbalance system described herein, a cam may be any structure or device that is set relative to a pivot of a joint, to exert a prescribed or variable motion on an interacting portion of a force generating device as a function of the rotation of the joint. More specifically, a cam refers to any structure or device that can convert rotational movement of a mechanical arm into a linear movement parallel to a longitudinal axis of a force generating device. Cams are preferably set eccentrically (i.e., not placed centrally or not having its axis or other part placed centrally) relative to a central axis of a pivot of a joint of a mechanical arm. A cam may be mounted within the circumference of a joint. Alternatively, a cam need not be mounted entirely within the circumference of a joint, and may readily be set outside the circumference of a joint where full rotation is unnecessary or where physical collision or interference of mechanical components is not a concern, for example as may be the case for large industrial robotic arms. Notably, full rotation may still be accomplished when the cam is positioned outside of the circumference of the joint. One example of a cam is an eccentric bearing, such as a bearing that is eccentric relative to a central joint or base pivot of an arm and/or one of the pivots of a parallelogram arm. A cam may also be approximated by a lever and bearing system, where, for example, the lever extends from a joint that can interact with a force generating device. Cams can be varied shape so as impart a desired linear deflection of the force generating device.

Any technique for achieving an interaction of a cam to its follower known in the art may be used to achieve interaction of a force generating device and a cam in the counterbalance assembly described herein. Each of the examples described in the Figures may be used to achieve an interaction between a force generating device and a cam. Still other forms of coupling using slots, pegs, pins or other techniques known in the art can be used to achieve the interaction of a force generating device and a cam. Interaction as used herein contemplates a force generating device abutting or engaging a cam, and a force generating device being linked or coupled to a cam.

There is a need in the art for apparatus and methods for exerting a force (e.g., to counteract the force of gravity) in order to reduce the physical effort exerted by users in various settings, including, but not limited to, medical professionals in performing medical examinations (e.g., ultrasound examinations). More particularly, there is a need in the art for an apparatus that can counterbalance a load for a user wherein the user can quickly and without additional effort pick up a payload with minimal effort.

An aspect of the present invention thereby preferably provides systems and methods to reduce the physical strain which may be experienced by users, including, but not limited to, medical practitioners who perform ultrasound examinations and similar medical procedures. It will be understood, however, that the present invention may be used to assist the performance of various tasks found in other settings, including, but not limited to, industrial environments.

A preferred embodiment of the counterbalance system described herein uses at least two resilient members with each resilient member interacting with at least one cam that is mounted eccentrically relative to a pivot of a joint of a mechanical arm. Functionally, the resilient member/cam relationships can be divided into first and second counterbalance assemblies. The purpose of each assembly is to generate torque. The torque generated by the first and second assemblies together allow the counterbalance system to maintain an equilibrium of torque exerted on a joint throughout the desired rotation of the joint. The torque provided by the first assembly is used to counteract the torque exerted by the mechanical arm and its associated payload at a rotational position, typically horizontal, where torque exerted by the arm is greatest. The torque provided by the second assembly is to counteract the linear change in force exerted by the first assembly. For example, the linear change in force due to linear displacement of resilient members in the first assembly when the arm is above horizontal results in the torque exerted by the mechanical arm being greater than the torque exerted by resilient member/cam pairs in the first assembly causing the arm to drift back to horizontal. In contrast, the linear change in force due to linear displacement of resilient members in the first assembly when the arm is below horizontal results in the torque exerted by the mechanical arm being less than the torque exerted by resilient member/cam pairs in the first assembly causing the arm to drift back to horizontal. The torque provided by the second assembly can maintain equilibrium when the arm is below and above the horizontal. Thus, the torque provided by the second assembly compensates for the first assembly to maintain the arm in positions other than the horizontal. The horizontal is the rest position, neutral position, or datum.

Counterbalance systems described herein may maintain equilibrium of torque for an unlimited degree of rotation. Torque equilibrium may be maintained for arm rotations greater than 1 degree, 45 degrees, 90 degrees, 135 degrees, 180 degrees, 225 degrees, 270 degrees, 315 degrees, 360 degrees, and even greater, in both positive and negative directions.

Counterbalance systems described herein may be used for one or more than one joint in a mechanical arm.

In order that the invention may be more fully understood, it will now be described, by way of example, with reference to the accompanying drawings in which FIG. 1 through FIG. 15 illustrate embodiments of the present invention.

Referring now to FIG. 1, there is a schematic illustration of a counterbalance system 100 in accordance with an embodiment of the present invention. The system 100 includes a counterbalance arm assembly 102 (alternately a first counterbalance assembly) linked with a preload assembly 104 (alternately a second counterbalance assembly). The system 100 further comprises a payload (K1) member 110, a payload compensation (K2) member 112 and an actuator compensation (K3) member 114. In some embodiments, the resilient members 110, 112, 114 are extension springs and are connected (e.g., pinned) such that the payload (K1) member 110 is employed in both assemblies 102 and 104. Those skilled in the art, however, will understand that the resilient members 110, 112, 114 may also be compression springs in alternate embodiments. An actuating arm 120 (alternately, an actuator) is in communication with a lifting arm 130 (a parallelogram comprising points A, B, F and I; alternately a payload arm), including a load coupler 132, for engaging a payload 10 to be held and/or moved. In a preferred embodiment, the load coupler 132 may move between points B and F.

Figure 2:
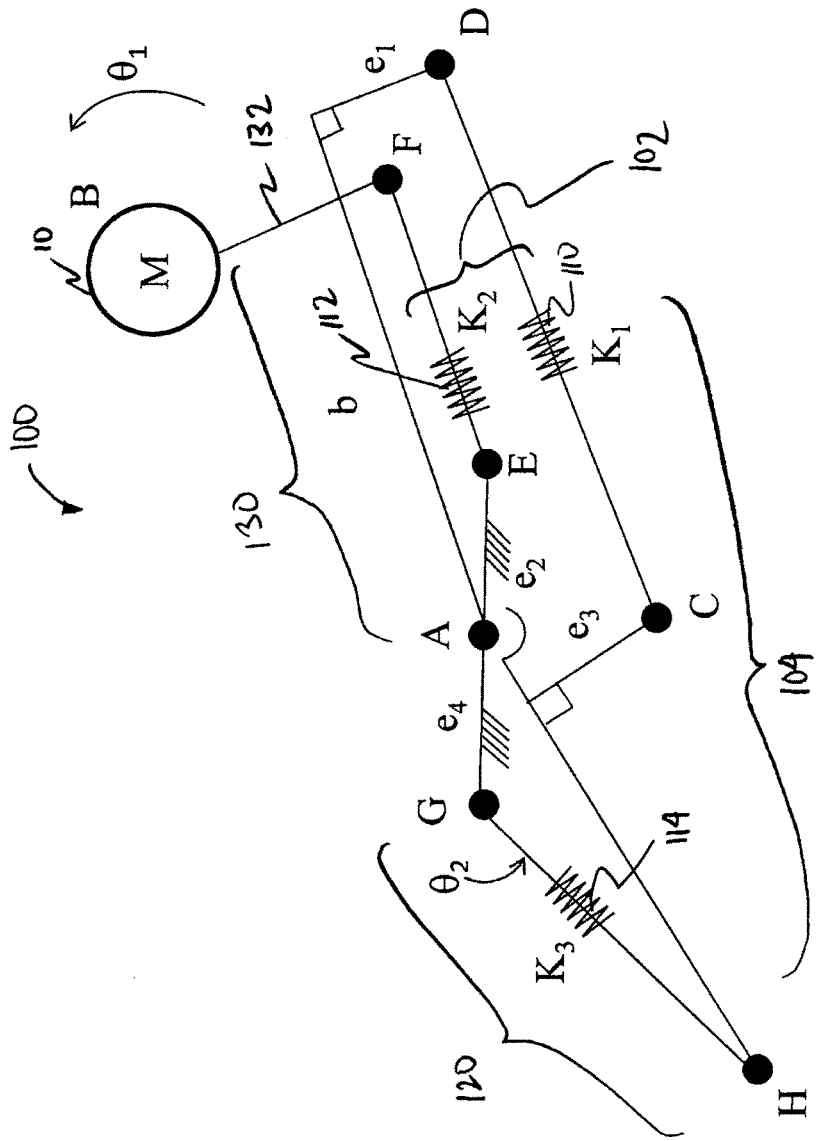
FIG. 2 is a schematic representation of a counterbalance system in a lever arm configuration with a payload.

Referring to FIG. 2, there is a schematic illustration of a counterbalance system 100 in accordance with an alternate embodiment of the present invention. The system 100 includes a counterbalance arm assembly 102 linked with a preload assembly 104. The system 100 further comprises a payload (K1) member 110, a payload compensation (K2) member 112 and an actuator compensation (K3) member 114. In some embodiments, the resilient members 110, 112, 114 are extension springs and are connected (e.g., pinned) such that the payload (K1) member 110 is employed in both assemblies 102 and 104. Those skilled in the art, however, will understand that the resilient members 110, 112, 114 may also be compression springs in alternate embodiments. An actuating arm 120 is in communication with a lifting arm 130 (a simple lever comprising points A and F), including a load coupler 132, for engaging a payload 10 to be held and/or moved.

As shown in FIGS. 1 and 2, assembly 102 includes the payload (K1) member 110 and the payload compensation (K2) member 112. The payload compensation (K2) member 112 is the compensating resilient member and the payload (K1) member 110 is the primary resilient member or the carrying member. The payload (K1) member 110 is responsible for supporting the weight of the payload 10 (or load vector). The payload (K1) member 110 and payload compensation (K2) member 112 work together to support the payload 10 by generating a lift vector. The payload compensation (K2) member allows the counterbalance force applied to the payload 10 to approximate a perfect counterbalance throughout the range of motion of the system 100.

As shown in FIGS. 1 and 2, the second counterbalance assembly 104 includes the payload (K1) member 110 and the actuator compensation (K3) member 114. In the assembly 104, the actuator compensation (K3) member 114 is the compensating resilient member and the payload (K1) member 110 is the primary resilient member for supporting the weight of the counterbalanced payload 10. Persons skilled in the art will understand that the actuator compensation (K3) member 114 does not impart a direct force to counterbalancing the payload 10 when actuator HG is locked and that the actuator compensation (K3) member 114 could be removed and the payload 10 would still be counterbalanced.

Figure 3:
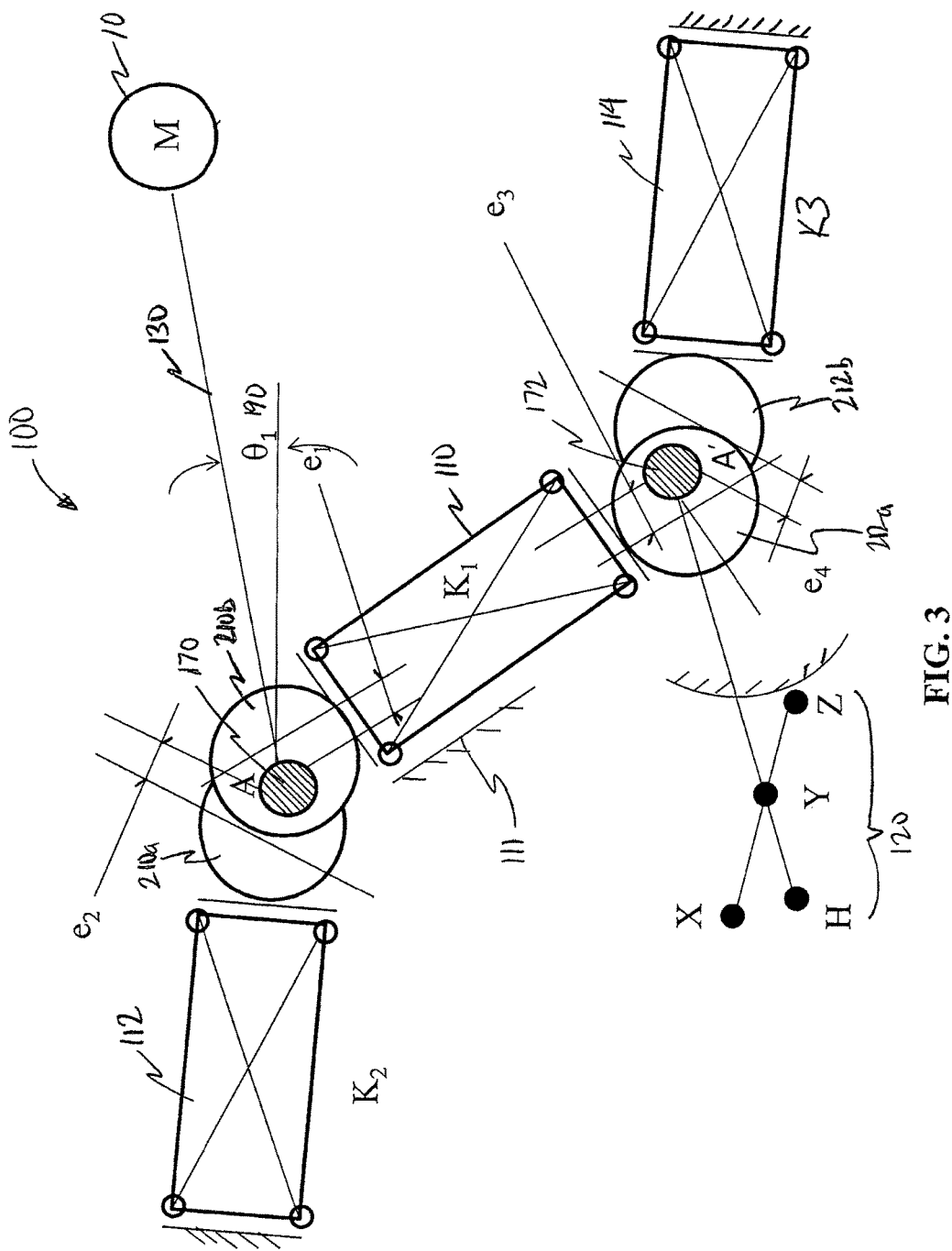
FIG. 3 is a schematic representation of a preferred embodiment of the counterbalance system of FIG. 2.

As shown in FIG. 3, the system 100 comprises resilient members 110, 112, 114 adapted to exert an expansion force (e.g., compression springs). The payload compensation (K2) member 112 and the actuator compensation (K3) member 114 are preferably fixed at a base (or grounded fixture) and the other end(s) may in communication with eccentric circular cams 210a and 212b—e.g., by a yoke (not shown)—such that each cam 210a, 212b is free to rotate about a fulcrum or pivot 170, 172 of a joint, and the resilient members 112, 114 are free to compress (or expand) to generate force. In preferable embodiments, the ends of the payload (K1) member 110 are not fixed and are free to engage cams 210b and 212a. The payload (K1) member 110 may preferably be axially constrained by a fixed guidance component 111 to maintain the alignment of the member 110 with the cams 210b, 212a. As will be seen in FIG. 3, cam 210b is eccentrically set relative to the pivot 170 of a joint by a distance equal to e1, and cam 210a is eccentrically set relative to the pivot 170 of the joint by a distance of e2. Similarly, cam 212a is eccentrically set relative to the pivot 172 of a joint by a distance equal to e3, and the fourth cam 212b is eccentrically set relative to the pivot 172 of the joint by a distance of e4.

As shown in FIG. 3, the payload (K1) member 110 interacts with cams 210b, 212a, while the payload compensation (K2) member 112 interacts with the first cam 210a, and the actuator compensation (K3) member 114 interacts with the fourth cam 212b. Cams 210ab are pinned to the payload arm 130 that supports the payload 10 and cams 212ab are pinned to the actuator 120. The compressive (or tensile) force exerted by each resilient member 110, 112, 114 results in a net torque being exerted about the first and second pivots 170, 172 of the payload arm 130 and actuator 120, respectively. It will be understood by a person skilled in the relevant art that there are numerous ways to connect or configure the payload (K1), the payload compensation (K2) and the actuator compensation (K3) members 110, 112, 114 in the preferred embodiments of the present invention. Referring to FIG. 3, for example, the resilient members 110, 112, 114 are abutting or adjacent to the payload arm 130 by associating each of the resilient members 110, 112, 114 with the one or more eccentric cams 210ab, 212ab. In a preferred embodiment, the resilient members 110, 112, 114 may slide against the surface of the cams 210ab, 212ab (and/or the cams 210ab, 212ab may roll against the ends of the resilient members 110, 112, 114) such that the point of contact of the resilient members 110, 112, 114 on the cams 210ab, 212ab may change as the payload arm 130 and/or the actuator 120 is rotated. In preferred embodiments, the payload (K1) member 110 is adapted for alignment with cams 210b, 212a using a guide (e.g., rail, cylinder) to facilitate sliding of the member 110 along its long axis. FIG. 3 is a schematic illustration depicting the geometric relationship of the resilient members 110, 112, 114 and cams 210ab, 210ab. Persons skilled in the art would understand that in this resilient member-cam relationship, the resilient members 110, 112, 114 exert an extension force (e.g., compression springs).

FIGS. 3 and 4 schematically illustrate different orientations of resilient members 110, 112, 114 and cams 210ab, 212ab in a system 100 designed to fully support the weight of a payload 10 about a hinged connection which is connected to a ground or stable fixture. As shown in FIG. 3, one end of resilient members 112 and 114 is anchored to the ground (or a fixture) while the lifting arm 130 (pinned to the cams 210ab) and/or the actuating arm 120 (pinned to the cams 212ab) are free to rotate about pivots 170, 172 of the joints of a mechanical arm. In preferable embodiments, the ends of the payload (K1) member 110 are not fixed and are free to engage cams 210b and 212a. Persons skilled in the art may understand that the ability to establish equilibrium of torque relative to pivots 170, 172 is not limited to the specific resilient member-cam orientations shown in FIGS. 3 and 4.

As shown in FIG. 3, the relationship between the payload (K1) member 110 and the second cam 210b to the lifting arm 130 is oriented such that the line joining the pivot 170 and e1 is not coincident with the line joining the pivot 170 to the center of gravity of the payload 10, which includes the mass of the lifting arm 130. Persons skilled in the art, however, may understand that as the value of $\theta_1$ is constantly changing, if the arm 130 is in a horizontal position, the line joining the pivot 170 and e1 will become coincident with the line joining the pivot 170 to the center of gravity of the payload 10.

In an example of an alternate orientation shown in FIG. 4, the relationship between resilient member 112 and the second cam 210b to the lifting arm 130 is orientated such that the line joining the pivot 170 and e1 is coincident with the line joining the pivot 170 to the center of gravity of the payload 10, which includes the mass of the lifting arm 130. Persons skilled in the art, however, may understand that as the value of $\theta_1$ is constantly changing, if the arm 130 moves away from a horizontal position, the line joining the pivot 170 and e1 will not be coincident with the line joining the pivot 170 to the center of gravity of the payload 10. Likewise, the line joining the pivot 172 and e3 is coincident with the line joining the pivot 172 to the center of gravity of the actuating arm 120. Persons skilled in the art, however, may understand that as the value of $\theta_2$ is constantly changing, if the arm 120 moves away from a horizontal position (H°), the line joining the pivot 172 and e3 will not be coincident with the line joining the pivot 172 to the center of gravity of the actuating arm 120.

In both FIGS. 3 and 4, the orientation of the relationship of the resilient members 110,112,114 to the cams 210ab, 212ab is preserved throughout the rotation of the arms 120, 130. Thus, if the cams are in a preferred position with respect to the pivots, that will define the orientation of the resilient member in space. If the resilient member is in a desired position in space, that will define the position of the cam with respect to the pivot. Referring to FIG. 3, there is depicted an example where the user may place the resilient members or cams in any orientation in space as long as the resilient member-cam pairs satisfy the equations provided in U.S. Patent Application No. 2010/0319164 (incorporated herein by reference).

Figure 4A:
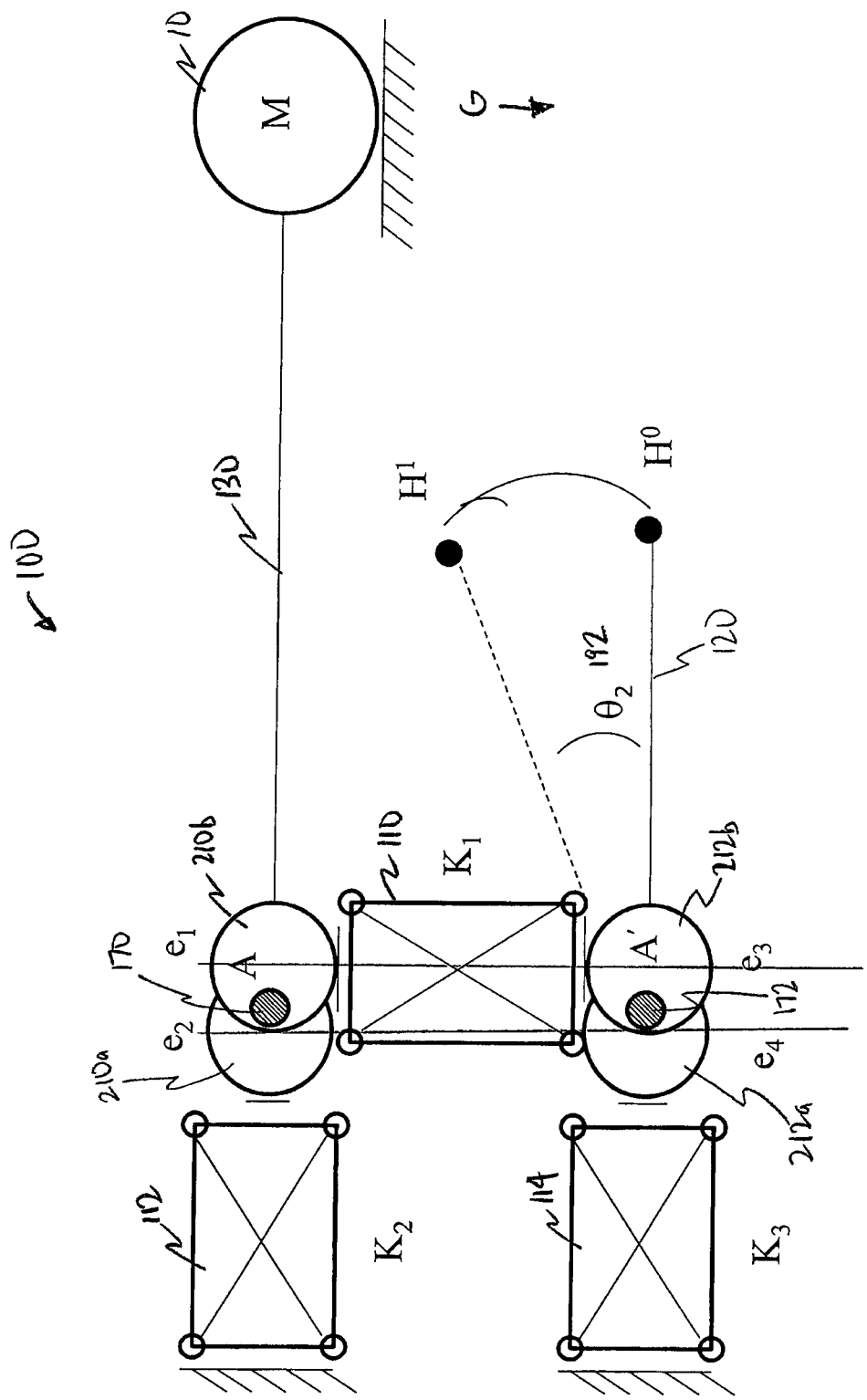
FIGS. 4A and 4B are schematic representations of the counterbalance system of FIG. 3 with the actuating arm at $H^0$ and $H^1$ respectively.

As shown in the configuration of FIG. 4A, given the orientation of the second cam 210b to the lifting arm 130, the resilient member 110 is preferably adapted for a vertical position. The payload (K1) member 110 preferably approximates a perfect balance of the payload 10 when the arm 130 is horizontal ($\theta_1$=0 degrees) and members 110, 112 are exerting a tensile force. However, persons skilled in the art may understand that given the configuration of the cams 210a,b, only the payload (K1) member 110 causes a rotational movement on the arm 130. As the arm 130 moves away from the horizontal, the counterbalance force from the payload (K1) member 110 no longer approximates a perfect counterbalance and the payload compensation (K2) member 112 is required to correct for this error. As the arm 130 rotates from horizontal, the payload (K1) member 110 will begin to exert a rotational moment on the arm 130 because of the cam 210b.

The relationship between the payload (K1) member 110 and the payload compensation (K2) member 112 and how they counterbalance the payload 10 is outlined in U.S. Patent Application No. 2010/0319164 (incorporated herein by reference). As shown in the in FIGS. 1 to 4, the present invention is a novel method to preload the payload (K1) member 110 quickly and easily for payloads having different and/or unknown weights. The purpose of the present invention is to avoid the user being required to set initial compression offsets.

In FIGS. 4A and B, the relationship between resilient member 112 and the first cam 210a to the lifting arm 130 is orientated such that the line joining the pivot 170 and e1 181 is coincident with the line joining the pivot 170 to the center of gravity of the payload 10, which includes mass of the lifting arm 130. Persons skilled in the art, however, may understand that as the lifting arm 130 rotates away from horizontal, the line joining the pivot 170 and e1 will not be coincident with the line joining the pivot 170 to the center of gravity of the payload 10. In preferable embodiments, the resilient member 112 may be aligned with the first cam 210a using a guide (e.g., rail, cylinder). In the specific example shown in FIGS. 4A and B, resilient member 112 is not adjustable, and is set by design such that the resilient member 112 exerts no load on the first cam 210a when the lifting arm 130 is in a vertical orientation (90 or 270 degrees relative to a Cartesian coordinate system where 0 degree corresponds to the positive X axis).

Still referring to FIGS. 4A and B, the relationship between each cam-resilient member pair is such that each cam is 180 degrees out of phase with each other (i.e., pivot 170 is in-between the eccentric points e1 181 and e2 182 and pivot 172 is in-between the eccentric points e3 183 and e4 184). In this configuration, each of the resilient members is constrained to be 90 degrees out of phase with each other (perpendicular). The relationship created from the constrained relationship between each resilient member/cam pair is the torque exerted by resilient member 112 leads, or lags, resilient member 110 by 90 degrees and the torque exerted by resilient member 112 leads, or lags, resilient member 114 by 90 degrees.

In an alternate embodiment, each resilient member/cam pair can be rotated about pivots 170, 172 to any position (for example, resilient members are aligned, 0 or 180 degrees) as long as the relationship between the cam and corresponding resilient member is maintained.

Thus, the ability to establish equilibrium relative to pivots 170, 172 is not limited to specific resilient member-cam orientations shown in FIGS. 3 and 4 as will also be apparent from equilibrium equations provided in the following paragraphs.

The following is a description of the equilibrium equations that govern the geometric resilient member/cam relationships shown in FIGS. 3 and 4. The force friction has been omitted from this analysis as it has no bearing on the equilibrium equations when the machine is at rest. Friction can be used as an advantage to construct inexpensive mechanisms that behave in a similar manner to the case illustrated in FIGS. 3 and 4 but do not fully balance the load. The sum of all the frictional forces between every moving part within the mechanism would prevent drift.

Referring to FIG. 3, equilibrium about the pivot 170 is established when the net torque is zero, i.e.:

$$T_g + T_x + T_y = 0 \quad (1)$$

where Tg is the unbalanced torque due to the payload 10, and the unbalanced torque produced from resilient members 110 and 112 are $T_x$ and $T_y$ respectively. The unbalanced torque produced by the weight is the product of the gravitational force due to the payload M, and the shortest distance between the force vector (M=mg) and the pivot 170:

$$T_g = Mr \cos(\theta_1) \quad (2).$$

Where "r" is the distance between the pivot 170 and the center of mass of the payload 10 and $\theta_1$ is the angle between horizontal (x-axis) and the line joining the center of gravity of the payload 10 and pivot 170.

The net torque of resilient member 110 about pivot 170 is equal to the sum of the torque produced from the compression of the resilient member due to the arm displacement $\theta_1$ 190 and the pre-compression of the resilient member 112 when the arm is horizontal (190: $\theta_1=0$), and is given by:

$$T_y = -(K_y e_1 \sin(\theta_1) + K_y \Delta y)(e_1 \cos(\theta_1)) \quad (3),$$

where $K_y$ is the resilient member 110 rate, and $\Delta y$ is the displacement of the resilient member from rest when the arm is horizontal. The net torque produced from resilient member 112 is given by:

$$T_x = K_x e_2^2 \cos(\theta_1)\sin(\theta_1) \quad (4),$$

where $K_x$ is the resilient member 112 rate and is uncompressed when the arm is in a vertical orientation (up or down). Substituting equations (2-4) into 1 gives the following:

$$Mr \cos(\theta_1) - K_y \Delta y e_1 \cos(\theta_1) + K_x e_2^2 \cos(\theta_1)\sin(\theta_1) - K_y e_1^2 \sin(\theta_1)\cos(\theta_1) = 0 \quad (5).$$

Equation 5 is equal to zero and independent of the angle $\theta_1$ under the following conditions:

$$Mr = K_y \Delta y e_1 \quad (6),$$

$$K_x e_2^2 = K_y e_1^2 \quad (7).$$

Equation 6 provides that resilient member 110 pre-compression $\Delta y$ is set to counterbalance the payload 10 at the arm position within the desired rotation where the torque exerted is greatest, typically when the arm is horizontal. Equation 7 provides the physical constraints which govern the relationship of each resilient member-cam pair.

Equation 5 can be expanded and written in the following form:

$$Mr \cos(\theta_1) - (K_{ya}\Delta y_a e_{1a} + K_{yb}\Delta y_b e_{1b} + \ldots)\cos(\theta_1) + (K_{xa}e_{2a}^2 + K_{xb}e_{2b}^2 + \ldots)\cos(\theta_1)\sin(\theta_1) - (K_{ya}e_{1a}^2 + K_{yb}e_{1b}^2 + \ldots)\sin(\theta_1)\cos(\theta_1) = 0 \quad (8).$$

Equation 8 is equal to zero and independent of the angle $\theta_1$ under the following conditions:

$$Mr = K_{ya}\Delta y_a e_{1a} + K_{yb}\Delta y_b e_{1b} + \quad (9),$$

$$K_{xa}e_{2a}^2 + K_{xb}e_{2b}^2 + \ldots = K_{ya}e_{1a}^2 + K_{yb}e_{1b}^2 + \quad (10).$$

From equations 9 and 10, the following illustrative embodiments are apparent:

The resilient member 110 and the second cam 210b can be replaced with multiple resilient member and cam assemblies.

If $(e_{1a}^2 = e_{1b}^2 = \ldots)$ and $(K_{ya} = K_{yb} = \ldots)$ then the resilient member 110 can be replaced by multiple resilient members acting against the second cam 210b.

The resilient member 112 and the first cam 210a can be replaced with multiple resilient member and cam assemblies.

If $(e_{2a}^2 = e_{2b}^2 = \ldots)$, and $(K_{xa} = K_{xb} = \ldots)$ then the resilient member 112 can be replaced by multiple resilient members acting against the first cam 210a.

If multiple resilient members are used in place of 110, then each resilient member can be preloaded a different amount to offset the payload when the arm is horizontal.

In FIGS. 3 and 4 when the illustrated mechanism is in balance, the torque exerted by the payload is equal and opposite to the torque exerted by the resilient members, regardless of the angular orientation of the arm 130. As illustrated in equation (7), this condition is met when the product of e1 squared and Ky is equal to the product of e2 squared and Kx. If e1 and e2 are equal, then both resilient members must have the same spring rate (Kx=Ky).

If tension springs are used in place of compression springs in FIG. 3, then placing the payload on the opposite side of the pivot (or rotating both cams 180 degrees), equilibrium about the pivot 170 is established when the net torque is zero, i.e.:

$$-T_g - T_x - T_y = 0 \quad (1),$$

where $-Tg$ is the unbalanced torque due to the payload 10, on the opposite side of the pivot 170 illustrated in FIG. 3, and the unbalanced torque produced from tension resilient member 110 and 112 are $-Tx$ and $-Ty$ respectively. The unbalanced torque produced by the weight is the product of the gravitational force due to the payload M, and the shortest distance between the vector (M) and the pivot 170:

$$-T_g = -Mr \cos(\theta_1) \quad (2).$$

The net torque of resilient member 110 about pivot 170 is equal to the sum of the torque produced from the extension of the resilient member due to the arm displacement 190 and the pre-tension of the resilient member when the arm is horizontal (190: $\theta_1=0$), and is given by:

$$T_y = +(K_y e_1 \sin(\theta_1) + K_y \Delta y)(e_1 \cos(\theta_1)) \quad (3),$$

where Ky is the resilient member rate of 110, and $\Delta y$ is the displacement of the resilient member from rest when the arm is horizontal. The net torque produced from resilient member 112 is given by:

$$T_x = -K_x e_2^2 \cos(\theta_1)\sin(\theta_1) \quad (4),$$

where Kx is the resilient member rate of 112 and is uncompressed when the arm is in a vertical orientation (up or down). Substituting equations (2-4) into 1 gives the following:

$$-Mr\cos(\theta_1)+K_y\Delta ye_1\cos(\theta)-K_x e_2^2\cos(\theta_1)\sin(\theta_1)+K_y e_1^2\sin(\theta_1)\cos(\theta_1)=0 \qquad (5).$$

Since this is equation 5, then it becomes apparent that tension-type resilient members can be used as a replacement for compression-type resilient members.

While the figures show counterbalance systems for a joint of a mechanical arm where the assembly comprises three resilient members, the skilled person having the benefit of reviewing the figures will recognize that the counterbalance assemblies need not be restricted to resilient member balance mechanisms and will further recognize equivalent counterbalance assemblies.

Figure 5:
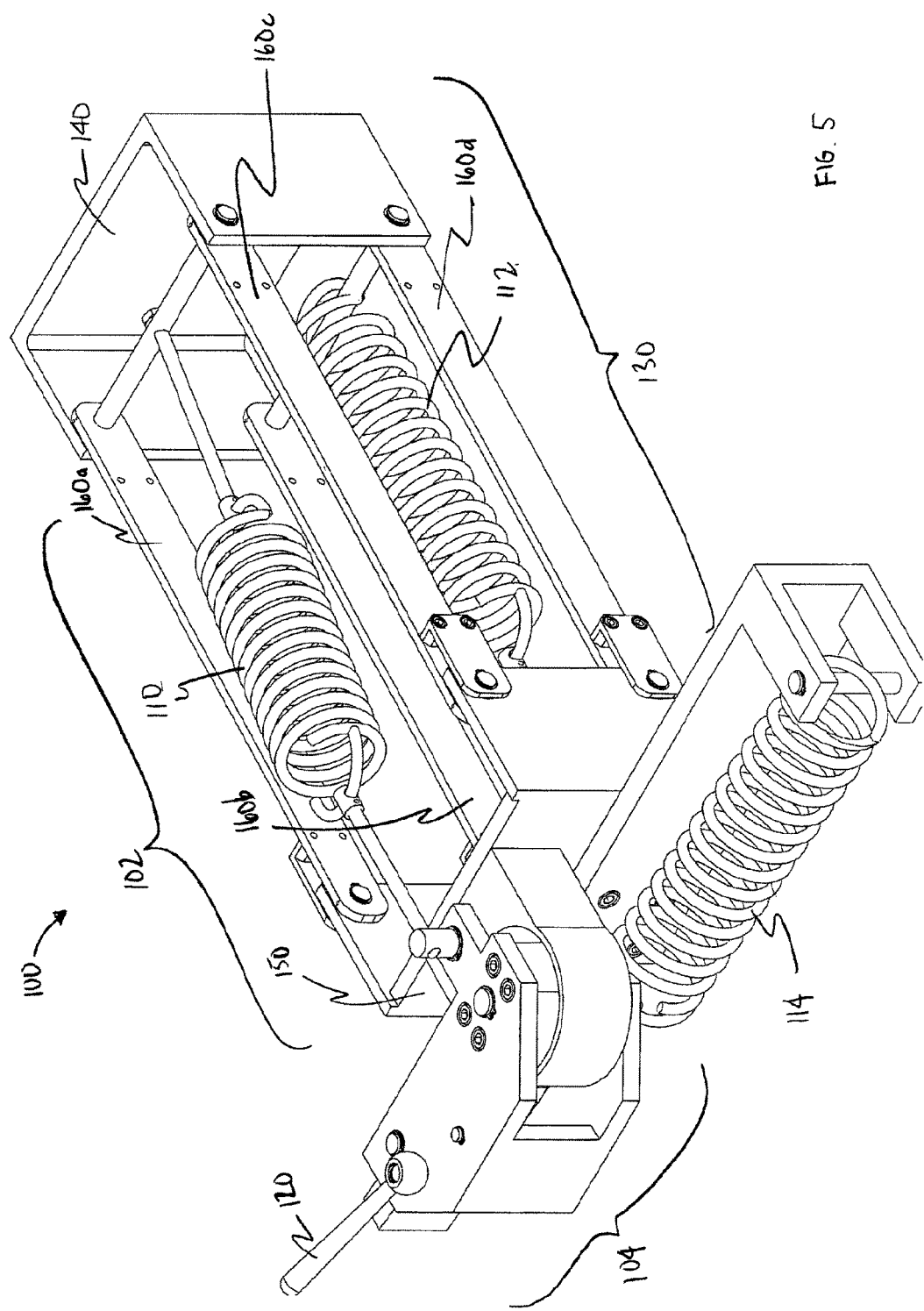
FIG. 5 is a perspective view of the counterbalance system of FIG. 1.

Other examples by which the resilient members can be connected are known to those skilled in the art. Specifically, instead of using the resilient member-to-cam interaction, the resilient members 110, 112, 114 may be connected using a pinned connection (as best shown in FIG. 5) at each end to the arm such that the pinned connection is offset from an arm pivot. This type of connection creates an eccentric relationship equivalent to the resilient member-to-cam embodiment described above (and shown in FIG. 3), as illustrated in FIG. 3 of U.S. Patent Application No. 2010/0319164 incorporated herein by reference, which doubles the stroke of the resilient member by allowing both tension and compressive loads while only compressing the resilient member in each case.

Referring to FIGS. 1, 2 and 3, the arm may be pivotally connected to the system via a pivot point or via a parallelogram linkage. Other means by which the arm can be connected to the system are known in to persons skilled in the art and include, for example, a spherical linkage (e.g., see FIG. 2 of Med. Phys., vol 35, no. 12, pp 5397-5410, 2008, incorporated herein by reference).

A user can adjust the carrying capacity of the lifting arm 130 with minimal effort. Persons skilled in the art would understand that if the first and second counterbalance assemblies 102,104 are modeled using the mechanism described in FIG. 1a of U.S. Patent Application No. 2010/0319164, then minimal effort would be required by the user to move the payload 10.

In operation, referring to FIGS. 1 to 4, a user can operate the counterbalance system 100 using the following steps:

The payload (K1) member 110 is uncompressed when the payload 10 is not supported by the lifting arm 130 (A-M) (FIG. 4A is a resting or neutral position before the load 10 is moved, whereby the payload compensation (K2) member 112 and the actuator compensation (K3) member 114 are charged and the actuator 120 is preferably adapted to transfer potential energy to the payload 10);

The payload compensation (K2) member 112 is uncompressed when $\theta_1$ 190 is equal to +/−90 degrees;

The actuator compensation (K3) member 114 is uncompressed when $\theta_2$ 192 is equal to +/−90 degrees;

$$K1^*(e_1^2)=K2^*(e_2^2); \text{ and}$$

$$K1^*(e_3^2)=K3^*(e_4^2).$$

Referring to FIG. 4A, there is illustrated a counterbalance system 100 with a payload 10 having unknown mass coupled to lifting arm 130 (alternatively referred to as beam AM 130). In this example, gravity (G) is pointing down, at a right angle to beam AM 130. Persons skilled in the art will understand that beam AM 130 does not have to be horizontal to pick up and/or support a payload 10. As shown in FIG. 4A, the actuator compensation (K3) member 114 is pre-compressed such that it becomes relaxed when the actuating arm 120 (alternatively referred to as handle A'H 120) is rotated plus/minus 90 degrees. As shown in FIG. 4A, the payload compensation (K2) member 112 is pre-compressed such that it becomes relaxed when the beam AM 130 is rotated so that the beam AM 130 is aligned with the force of gravity (G). As shown in FIG. 4A, the payload (K1) member 110 is uncompressed at the same time the actuator compensation (K3) member 114 is compressed to its maximum extent.

To pick up a payload 10, the user rotates the handle A'H 120 counterclockwise from $H^0$ to $H^1$. If $K1^*(e_3^2)=K3^*(e_4^2)$, the user will feel little to no perceivable resistance because the potential energy from the actuator compensation (K3) member 114 is redirected to the payload (K1) member 110 as a preload, which is equal to $K1^*e_3^*\sin(\theta_2)$.

At the point when the payload (K1) member 110 is completely supporting the payload 10, the user will feel an increasing resistance when trying to rotate the handle A'H 120 beyond point $H^1$.

Figure 4B:
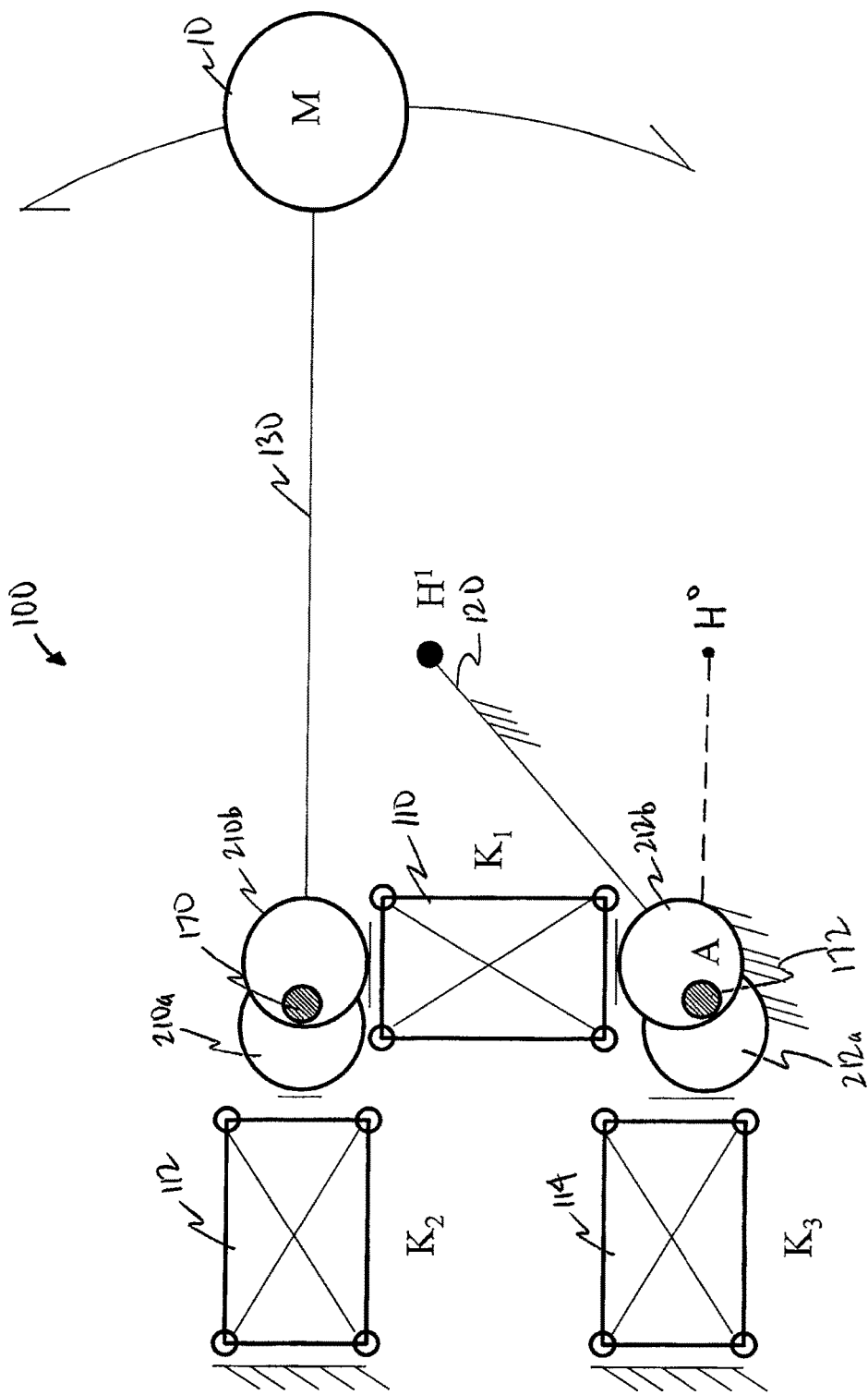

Referring to FIG. 4B, if the handle A'H 120 is secured in position $H^1$, the payload 10 will be fully supported by the payload (K1) member 110 and the payload compensation (K2) member 112 if $K1^*(e_1^2)=K2^*(e_2^2)$. In some preferred embodiments, the beam A'H 120 may be secured using a brake (as best shown in FIGS. 11 to 13) that will not release unless the arm A'H 120 is in a safe position, as best illustrated in FIG. 3 as lever XYZ. The braking mechanism is a self-locking brake. The brake is preferably required for the system 100 to operate. If the rotation of A'H 120 is not restricted by the brake, arm A'H 120 will rotate and cause the counterbalance force to be lost (i.e., the energy stored in the payload (K1) member 110—for example, support energy—will be transferred back into the actuator compensation (K3) member 114).

Still referring to FIG. 3, if the angle XYH is less than the critical value, which is typically about 7 degrees and depends on the brake and the drum material, no actuation force needs to be applied for braking. Also, the brake will not slip and cannot be released by the user if there is a difference in the current energy level of the payload 10 and the point where the payload 10 is picked up. This will prevent the user from releasing the payload 10 when it is unsafe to do so. The range of motion is 360 degrees provided that the payload (K1) member 110 and the payload compensation (K2) member 112 have enough stroke to allow for this motion. If the counterbalance system 100 is more compact, then the stroke will be shortened thereby limiting the range of motion. As long as the payload (K1) member 110 and payload compensation (K2) member 112 are not over-compressed, a full 360 degrees range of motion is possible.

As can be seen in FIGS. 3 and 4, the relationship between the cams 210ab, 212ab and eccentrics e1,e2,e3,e4 is preferably the same for the first counterbalance assembly 102 and the second counterbalance assembly 104. In operation, rotation of the actuating arm 120 will cause the force exerted by the payload (K1) member 110 and the actuator compensation (K3) member 114 to change, while the force exerted by the payload compensation (K2) member 112 remains unchanged. Rotation of the lifting arm 130 will cause the force exerted by the payload (K1) member 110 and the payload compensation (K2) member 112 to change, while the force exerted by the actuator compensation (K3) member 114 remains unchanged. As the first cam 210a is 90 degrees out of phase with the second cam 210b, and the third cam 212a is 90 degrees out of phase with the fourth cam 212b, movement of the load 10 (having a load vector) attached to the lifting arm 130 transfers energy between the payload (K1) member 110 and the actuator compensation (K3)

member 114 and movement of the actuating arm 120 transfers energy between the payload (K1) arm 110 and the payload compensation (K2) arm 112. The direction of energy flow preferably depends on the direction of rotation of the actuating arm 120 and the lifting arm 130. For example, if the load 10 is lifted, then both the payload (K1) member 110 and the payload compensation (K2) member 112 will lose energy (for example, support energy) to the payload 10. In some embodiments, the transfer of energy (for example, actuator energy) between the actuator compensation (K3) member and the payload (K1) member may be prevented by engagement of a brake 122 (as best seen in FIGS. 11 to 13). As the system 100 is preferably a closed system, the sum of the potential energy of the members 110, 112, 114 and the load 10 is a constant (i.e., $PE_{(K1)member} + PE_{(K2)member} + PE_{(K3)member} + PE_{load} =$ constant).

FIG. 5 shows an alternate embodiment of the system 100 of the present invention in which the resilient members 110, 112, 114 are extension springs. As before, the system 100 may be divided into a counterbalance arm assembly 102 and a preload assembly 104. The system 100 shown consists of a forward base plate 140, a rear base plate 150, and four stabilizing members 160abcd which form a parallelogram linkage. The lifting arm 130, accordingly, consists of a single parallelogram segment and preferably contains two resilient members 110, 112. As in the previous design, the payload (K1) member 110 may be adjustable to support payloads 10 of different weights and the payload compensation (K2) member 112 preferably corrects errors in the payload (K1) member 110 as the arm 130 moves through its full range of motion. The two resilient members 110, 112 are preferably mounted eccentrically with a 90 degree shift.

Figure 6A:
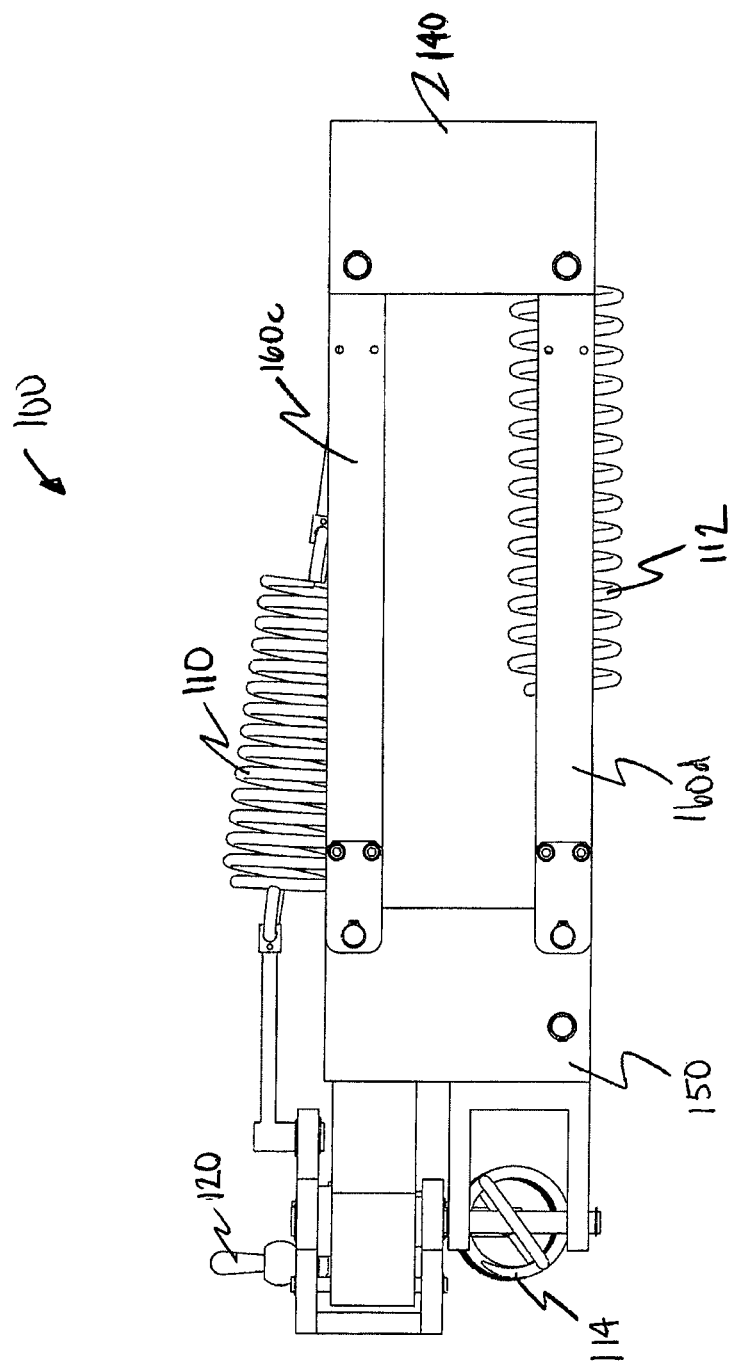
Figure 6B:
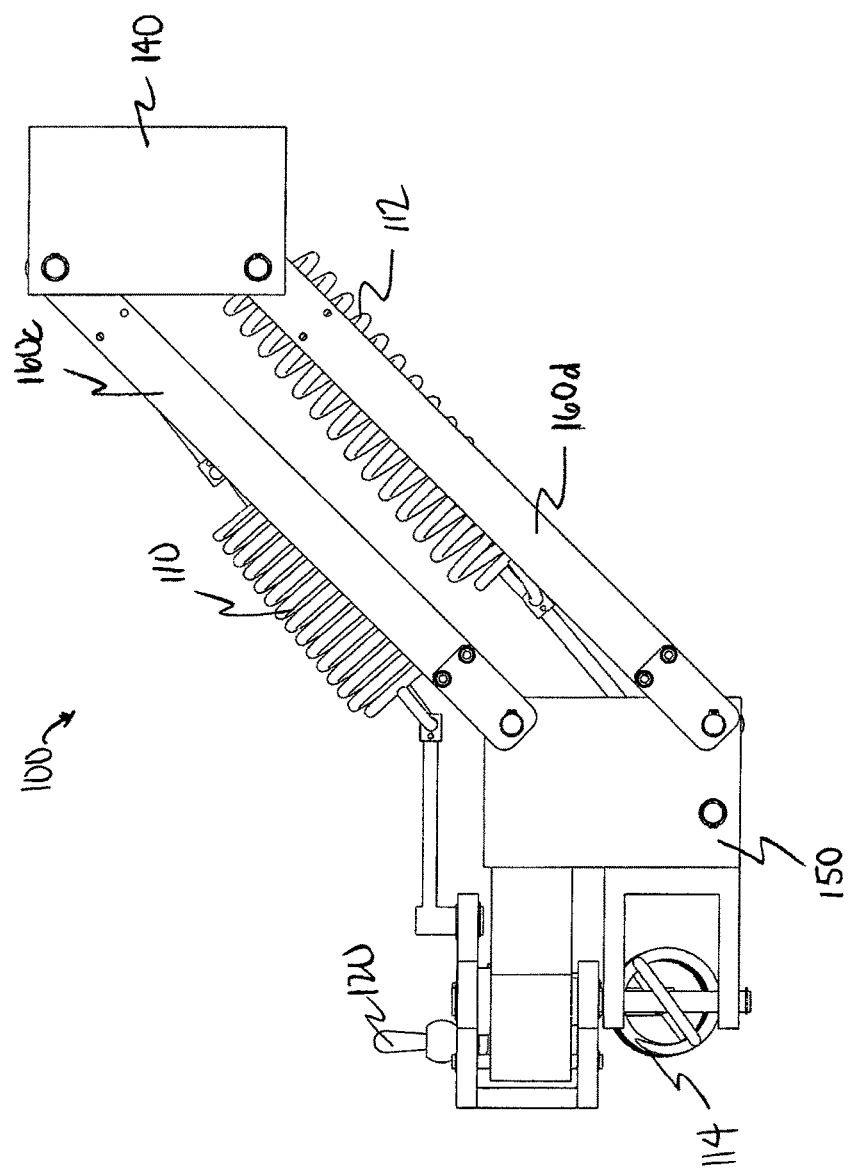

FIGS. 6A, 6B, and 6C demonstrate the range of motion of the lifting arm 130. As shown in FIG. 6A, when the system 100 is in a neutral state (i.e., neither lifting nor lowering a payload 10), the payload (K1) member 110 is preloaded and the payload compensation (K2) member 112 is at a maximum extension. Persons skilled in the art, however, will understand that due to the eccentricity, the payload compensation (K2) member 112 is exerting zero moment on the arm 130. As shown in FIG. 6B, when the system 100 is used to lift a payload 10 (not shown) into a load-bearing position, the payload (K1) member 110 is compressed and the payload compensation (K2) member 112 is compressed. As shown in FIG. 6C, when the system 100 is used to lower a payload 10 (not shown) in the load-bearing position, the payload (K1) member 110 is extended and the payload compensation (K2) member 112 is compressed.

Figure 7:
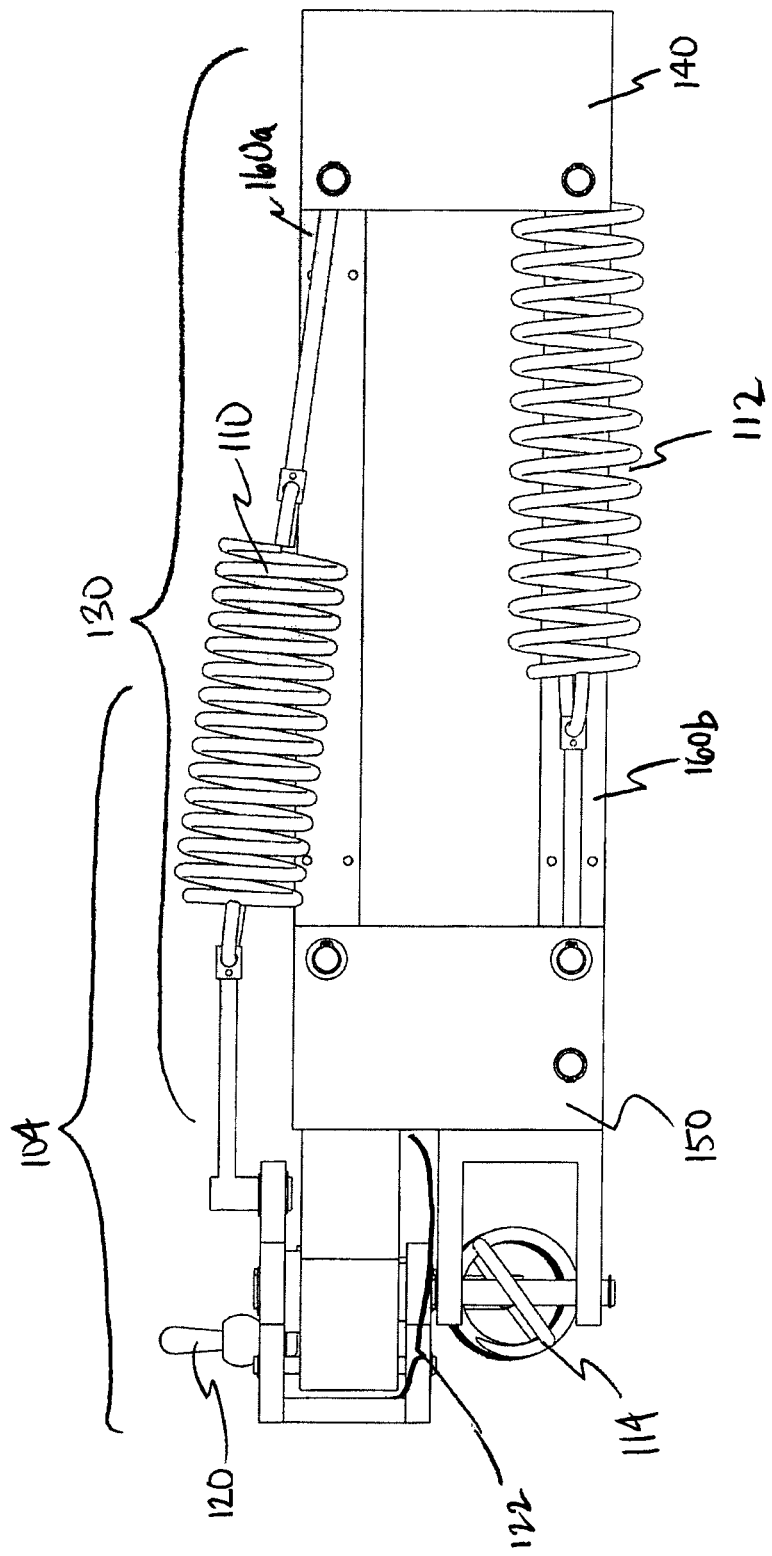
FIG. 7 is a side cross-sectional view of the system of FIG. 5.

FIG. 7 shows a side view of the arm 130 in cross-section to better view the relationship of the payload (K1) member 110 to the payload compensation (K2) member 112.

In the present embodiment, the method of preloading the payload (K1) member 110 is novel. In the prior art, the resilient member 110 may have been preloaded using a wrench to turn a preload nut. In the system 100 of the present invention, the payload (K1) member 110 is preloaded using a preload assembly 104 (also known as the second counterbalance assembly). One end of the payload (K1) member 110 is attached to the forward base plate 140 and one end is attached to the preload assembly 104. Previously, the adjustable payload (K1) member 110 was attached between two base links (not shown). The payload (K1) member 110 is attached eccentrically to the actuator 120 of the preload assembly 104. The payload (K1) member 110 has zero preload when the preload assembly 104 is at its home position ($H^0$) (also referred to as the unloaded position; not shown) and maximum preload when the preload assembly 104 has rotated 180 degrees ($H^1$) (also referred to as the loaded position; not shown). Rotating the preload assembly 104 counterclockwise will draw the payload (K1) member 110 back to preload it and increase the payload capacity of the arm 130.

Figure 8A:
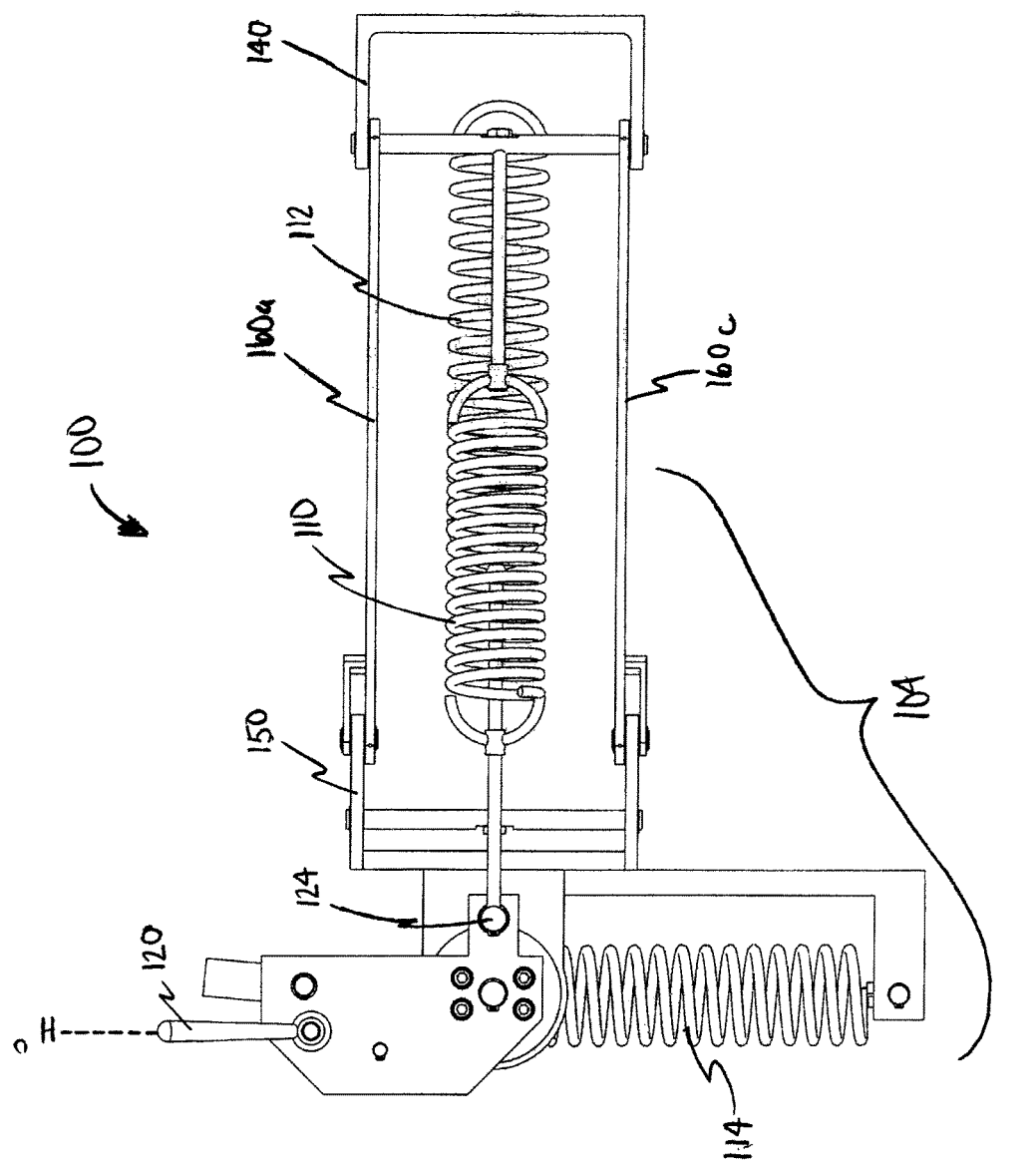
FIGS. 8A and B are top views of the system of FIG. 5 with the actuating arm at $H^0$ and $H^1$ respectively.
Figure 8B:
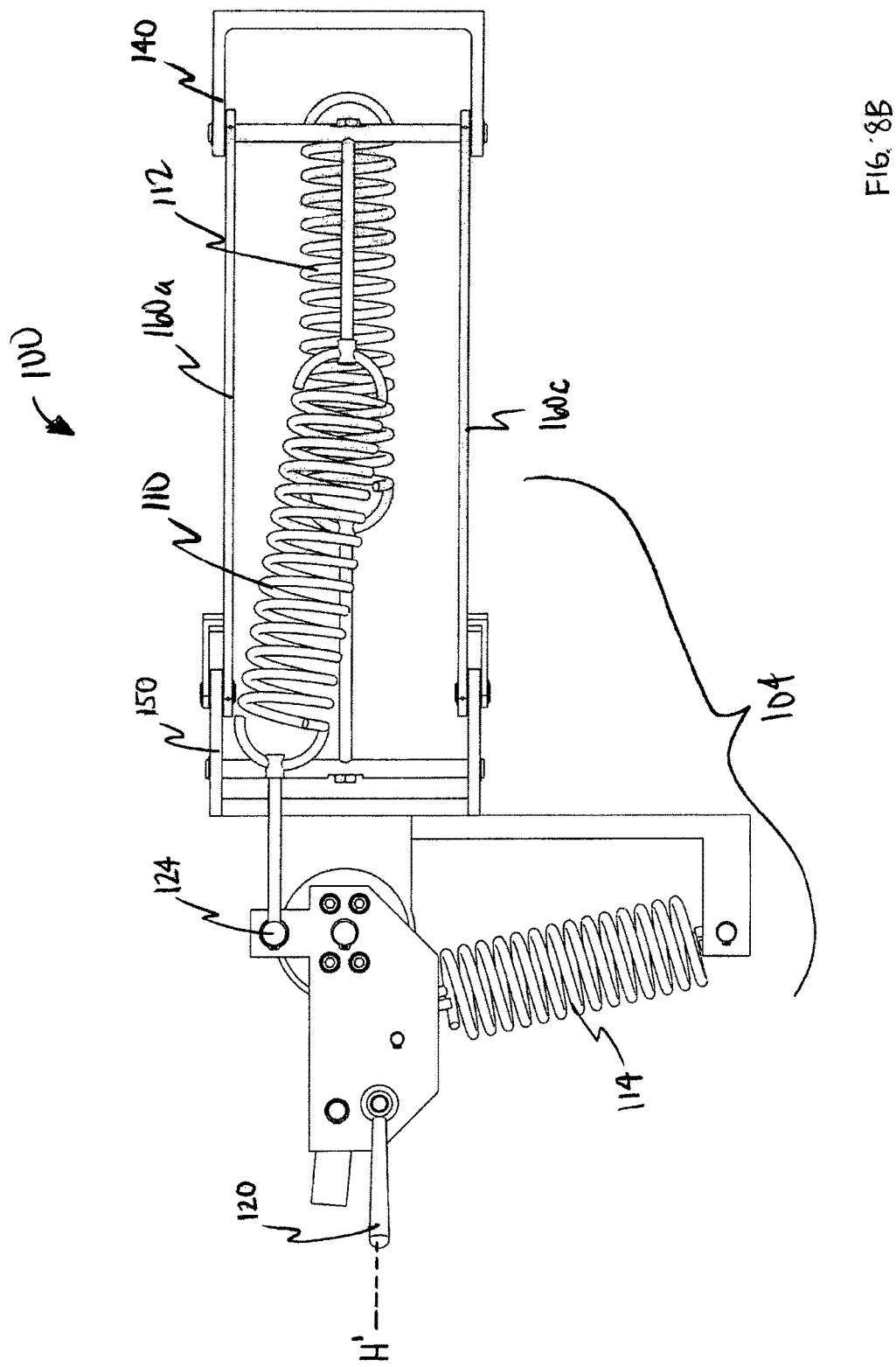

FIGS. 8A and 8B show the preload assembly 104 rotating 90 degrees from its unloaded position ($H^0$) to preload the payload (K1) member 110. The preload distance of the payload (K1) member 110 is dependent on the eccentric sizing of the resilient member attachment point 124 on the actuator 120. If the preload assembly 104 is rotated 90 degrees the preload distance is equal to the eccentric size. If the preload assembly 104 is rotated 180 degrees the preload distance is approximately equal to twice the eccentric size. The preload assembly 104 prevents the actuator 120 from rotating clockwise in order to maintain the preload and prevent the payload (K1) member 110 from unloading.

As the preload assembly 104 is rotated, the user may experience increasing resistance from the payload (K1) member 110 as it extends. If the member 110 is extremely stiff, the user will be required to exert a significant amount of force and may experience difficultly in rotating the actuator 120. The addition of the actuator compensation (K3) member 114 allows the user to rotate the actuator 120 with a minimal level of exertion. The actuator compensation (K3) member 114 is preferably mounted perpendicularly to the first and second resilient members 110, 112. The actuator compensation (K3) member 114 is attached to the actuator 120 eccentrically. The eccentric for the actuator compensation (K3) member 114 is shifted 90 degrees from the eccentric for the payload (K1) member 110. The actuator compensation (K3) member 114 acts to counterbalance the force of the payload (K1) member 110 on the actuator 120 and considerably reduces the force the user must exert to preload the payload (K1) member 110.

The principals and equations governing the relationship between the payload (K1) member 110 and the actuator compensation (K3) member 114 are preferably, but need not necessarily, exactly the same as the relationship between the payload (K1) member 110 and the payload compensation (K2) member 112. To achieve counterbalancing of the payload 10 and minimal user exertion during payload (K1) member 110 preloading the following relationship must be true:

$$K_{K1}*(e_{K1})^2 = K_{K2}*(e_{K2})^2 \qquad (1);$$

and $$K_{K1}*(e_{K1})^2 = K_{K3}*(e_{K3})^2 \qquad (2),$$

where "K" is the respective resilient member constants of the different members 110, 112, 114 and "e" is the respective resilient member eccentricities of the different members 110, 112, 114. The resilient member eccentricities of the arm are identified in FIGS. 1 to 4.

FIG. 9 depicts a bottom plan view of the system 100. The resilient members 110, 112, 114 are shown, notably including the actuator attachment point 126, which may define an eccentricity, for the actuator compensation (K3) member 114.

As seen in FIG. 10, there is an enlarged cross-sectional view of the actuator 120, a handle member 116 and the actuator compensation (K3) member 114. Member 116 is preferably used to automatically lock the brake 122 to prevent the actuator 120 from moving away from position $H^1$.

Figure 11A:
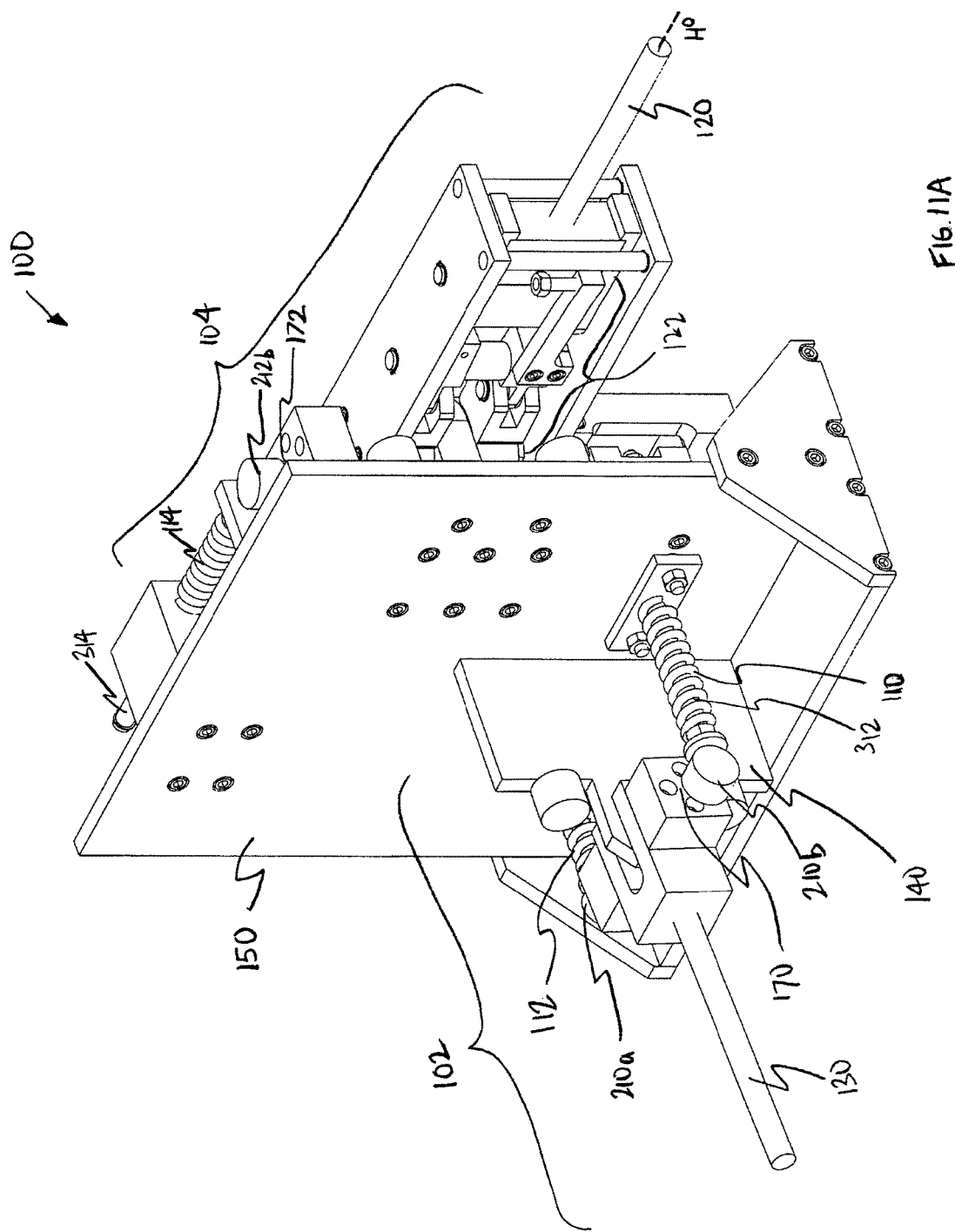
FIGS. 11A and B are a front and rear perspective view, respectively, of the system of FIGS. 3, 4A and B with the actuating arm at $H^0$.
Figure 11B:
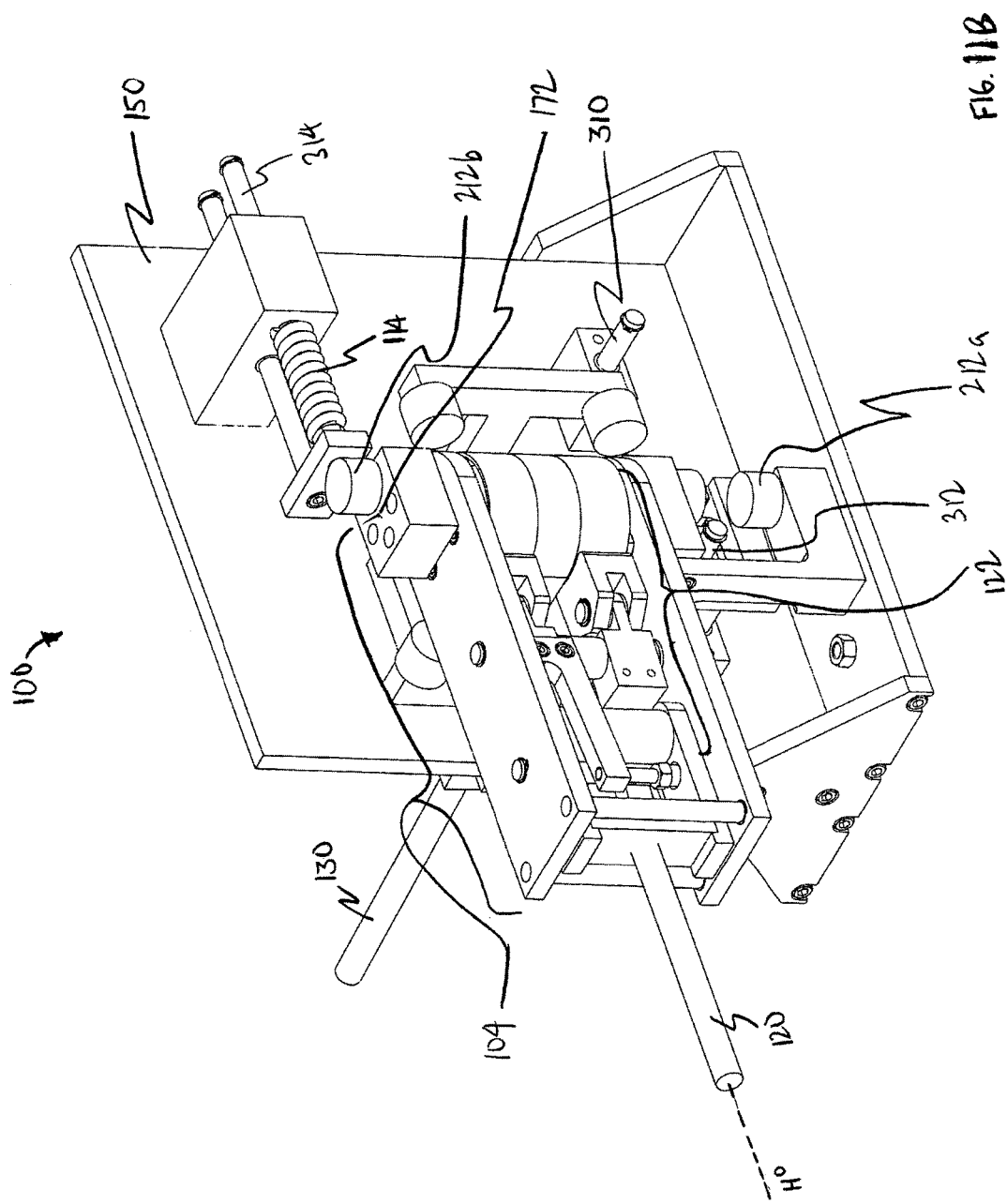

Referring to FIG. 11A, there is depicted a preferred embodiment of the system 100 as described schematically in FIGS. 3 to 4, in which the resilient members 110,112,114 are compression springs. As previously, the system 100 may be divided into a counterbalance arm assembly 102 (or first counterbalance assembly) and a preload assembly 104 (or second counterbalance assembly). The system 100 shown consists of a forward base plate 140 and a rear base plate 150. The lifting arm 130 (or payload arm) is in communication with the payload (K1) and payload compensation (K2) members 110, 112. The payload (K1) and payload compensation (K2) members 110, 112 are mounted on first and second posts 310 (as seen in FIG. 11B), 312 respectively. Cams 210ab abut member 112 and 110 respectively. The payload (K1) member 110 may be adjustable to support payloads 10 of different weights and the payload compensation (K2) member 112 preferably corrects errors in the member 110 as the arm 130 moves through its full range of motion about pivot 170.

Also seen in FIG. 11A is the second counterbalance assembly 104, which extends from the rear base plate 150 and includes the third resilient member 114 mounted on a third post 314. Cam 212b abuts member 114. The second counterbalance assembly 104 may preferably, but need not necessarily, be moved about pivot 172 using the actuating arm 120 (or actuator), which may also be used to engage and/or disengage the brake 122.

The second counterbalance assembly 104 of this preferred embodiment is best depicted in FIG. 11B. The second assembly 104 comprises the actuator compensation (K3) member 114 supported by the third post 314 and adapted to interact with the fourth cam 212b which is mounted eccentrically relative to the second pivot 172. The second assembly 104 may be rotated about the second pivot 172 using the actuating arm 120 (which is in the non-payload engaging, unloaded, or $H^0$ position) and reversibly locked in position by the brake 122. As previously mentioned, the second assembly 104 also comprises the payload (K1) member 110 (not shown), supported by the second post 312 (not shown), which is in communication with the third cam 212a mounted eccentrically relative to the second pivot 172.

FIGS. 12A and B depict the system 100 (as shown in FIGS. 11A and B) from a rear and front perspective respectively, whereby the second counterbalance assembly 104 has been rotated about the second pivot 172 to a payload engaging, or loaded, position ($H^1$). The actuator compensation (K3) member 114 expands as the cam 212b rotates about pivot 172. Payload (K1) member 112 compresses as cam 212a rotates about pivot 172 and the second post 312 is pressed against cam 210b.

FIG. 13 depicts the system 100 (as shown in FIGS. 11A and B) from a front perspective with the lifting arm 130 rotated vertically about the first pivot 170. The payload (K1) member 110 expands as the lifting arm 130 is raised and the cam 210b rotates about pivot 170.

Figure 14A:
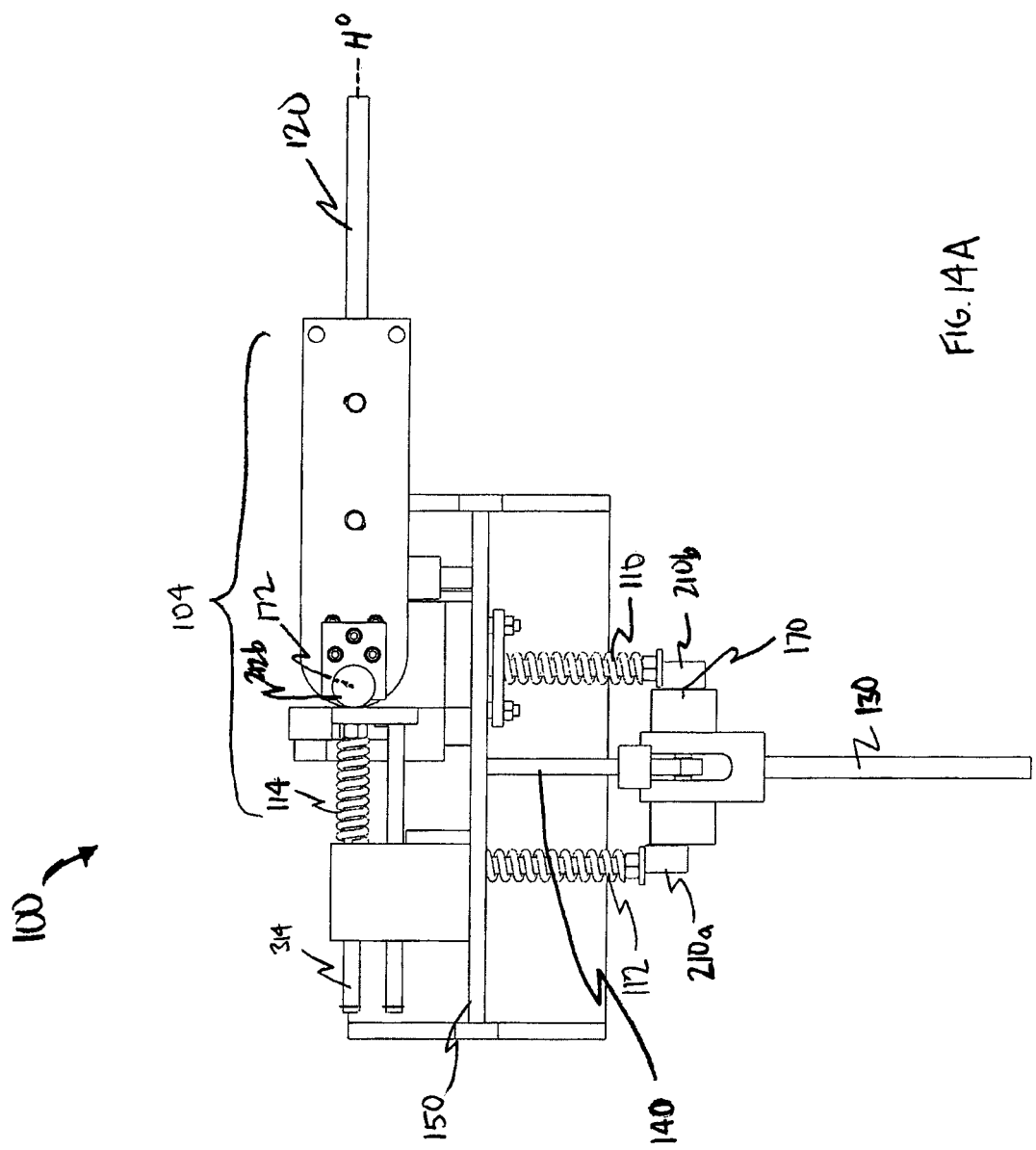
FIGS. 14A and B are plan views of the system of FIGS. 11A and B and FIGS. 12A and B respectively.

FIGS. 14A and B show a top view of the system 100 (as shown in FIGS. 11A and B) with the second assembly 104 in a non-payload, unloaded, engaging (i.e.,) $H^0$ and payload, or loaded, engaging (i.e., $H^1$) position respectively. The second assembly 104 is rotated about the second pivot 172. The actuator compensation (K3) member 114 expands as the cam 212b rotates about pivot 172 due to rotation of the handle 120 between $H^0$ and $H^1$. Payload (K1) member 112 compresses as cam 212a (not shown) rotates about pivot 172 and the second post 312 is pressed against cam 210b.

Figure 15A:
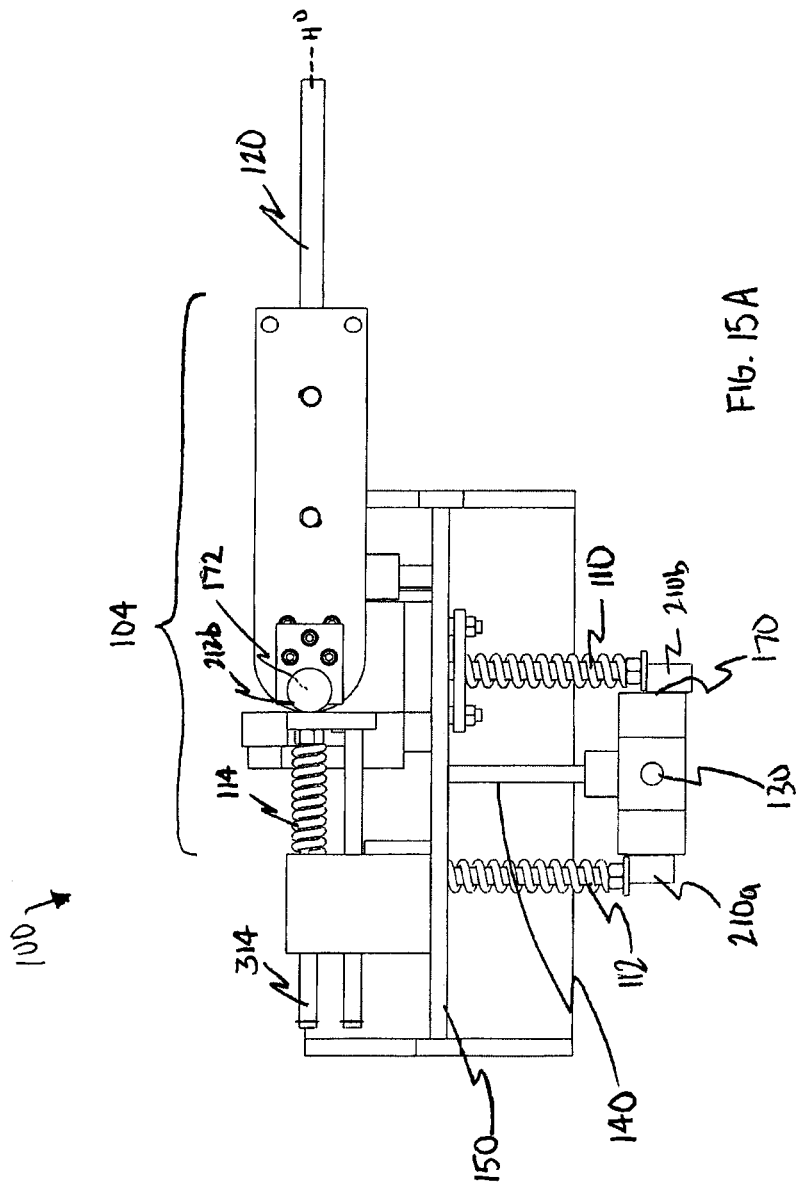
FIGS. 15A and B are plan views of the system of FIGS. 11A and B with the actuating arm at $H^0$.
Figure 15B:
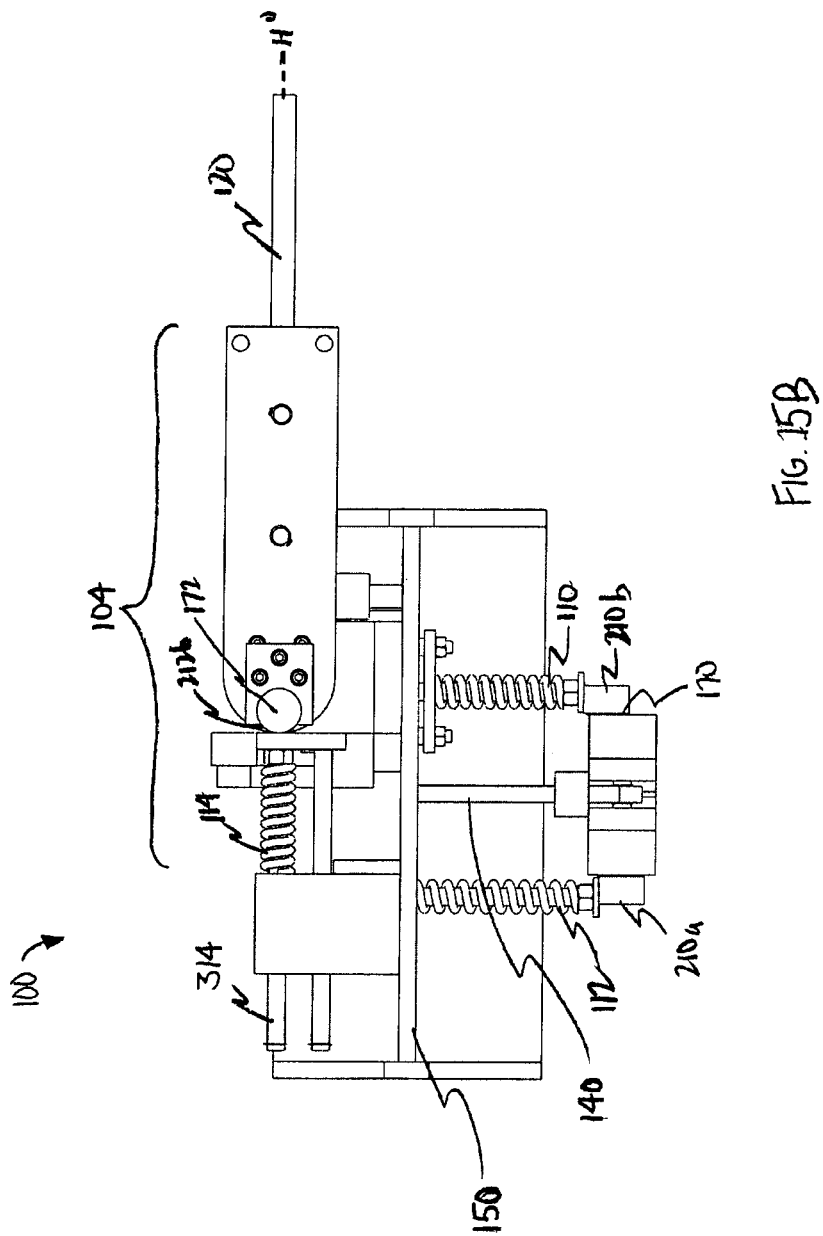

FIGS. 15A and B depict a top view of the system 100, with the second assembly 104 in a non-payload engaging (i.e.,$H^0$ and the lifting arm 130 extending out from the page and in to the page, respectively. Actuator 120 is in the $H^0$, or unloaded, position and the payload arm 130 is positioned along the z-axis (i.e., out from and into the page, respectively) to demonstrate the compression of the payload (K1) member 110 due to rotation of the cam 210b about the pivot 170.

Figure 12B:
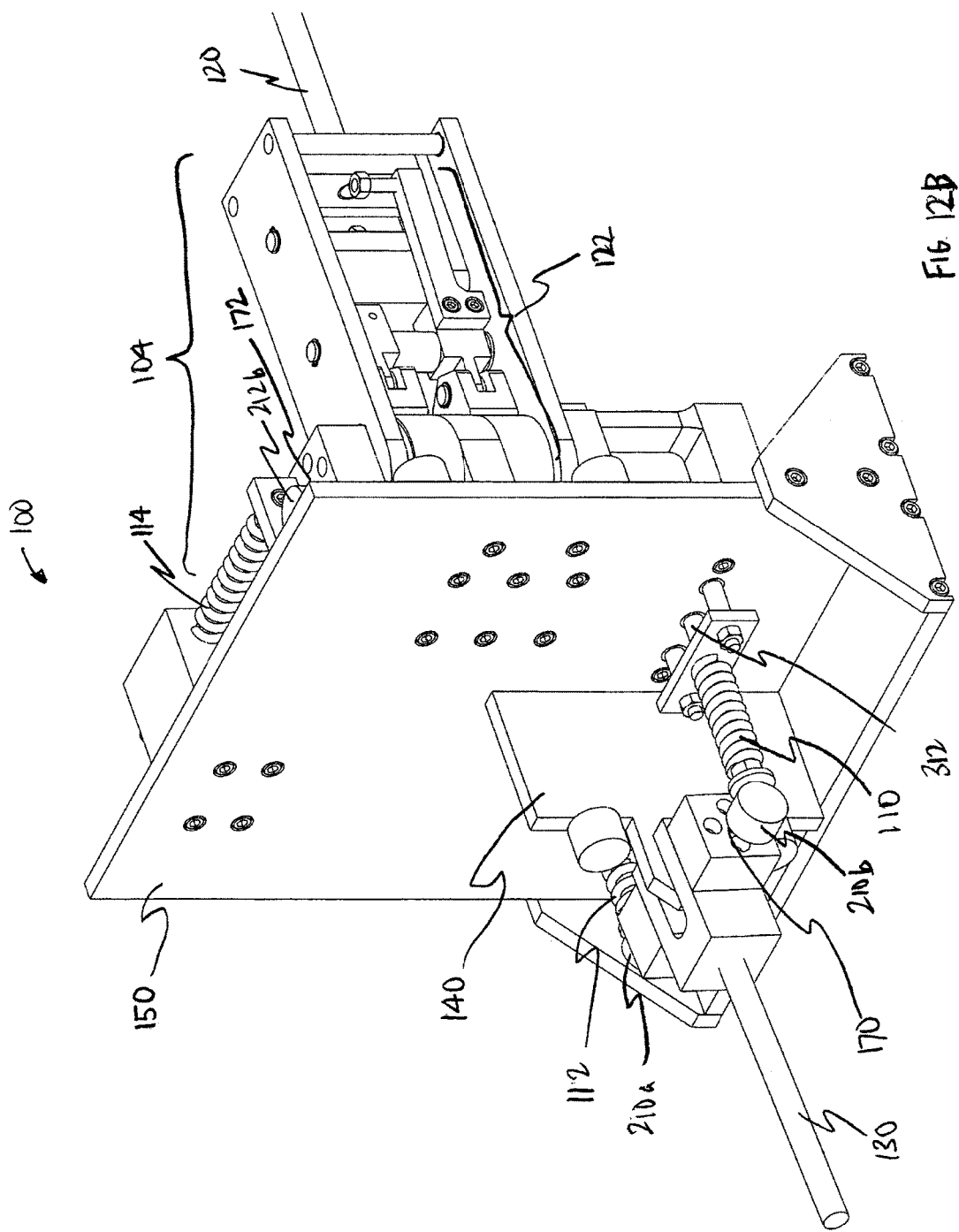
FIGS. 12A and B are a rear and front perspective view, respectively, of the system of FIGS. 11A and B with the actuating arm at $H^1$.
Figure 13:
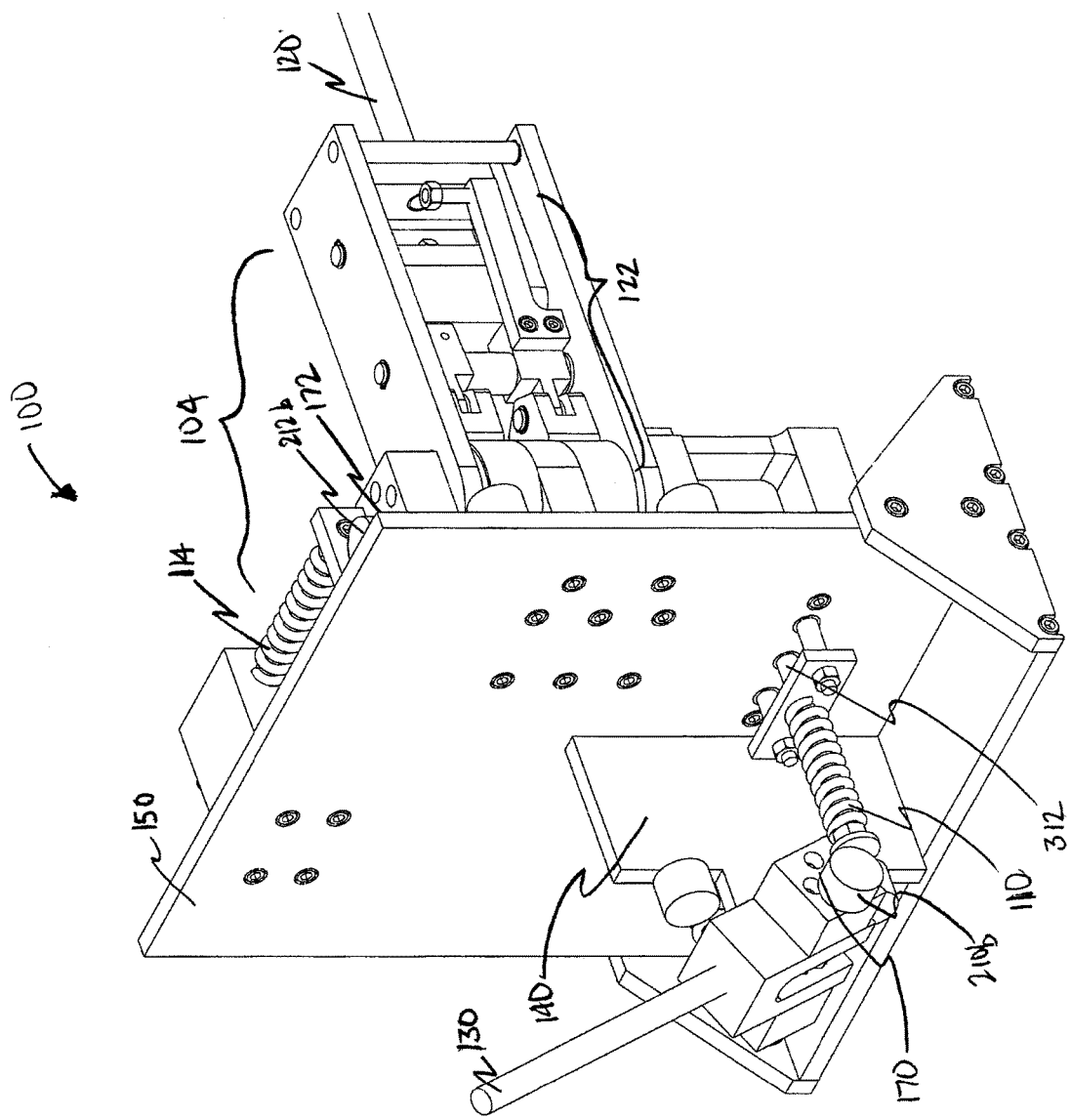
FIG. 13 is a front perspective view of the system of FIGS. 12A and B with the lifting arm raised.

With reference to FIGS. 8B and 12B, to preload the payload (K1) member 110 the user preferably rotates the actuator 120 counterclockwise. The user will preferably be required to exert a minimal level of force until the payload (K1) member 110 is sufficiently preloaded to counterbalance the payload 10 coupled to the lifting arm 130. The user may experience a sudden increase in resistance turning the actuator 120 when sufficient preload has been achieved. The user can release the actuator 120 and the brake (as best shown in FIG. 11B) will lock the actuator 120 in place, preventing the payload (K1) member 110 from pulling the actuator 120 to release all energy stored in the actuator compensation (K3) member 114.

As shown in FIGS. 11A to 15B, the first cam 210a is 90 degrees out of phase with the second cam 210b (i.e., the first pivot 170 is in between the corresponding eccentric points schematically shown in FIGS. 3 and 4) and the third cam 212a is 90 degrees out of phase with the fourth cam 212b (i.e., the second pivot 172 is in between the corresponding eccentric points schematically shown in FIGS. 3 and 4). Accordingly, when the actuator 120 is in the non-load engaging position $H^0$ (and the payload arm 130 is in a horizontal position), the first (K2) resilient member 110 is compressed, the second (K1) resilient member 112 is relaxed, and third (K3) resilient member 114 is compressed. When the actuator 120 is in the load engaging position $H^1$ (and the payload arm 130 is in a vertical position), the first (K2) resilient member 110 is relaxed, the second (K1) resilient member 112 is compressed, and the third (K3) resilient member 114 is relaxed.

FIG. 11B depicts the tripping mechanism or brake 122. The brake 122 is preferably, but need not necessarily, a friction-based toggle design or any other braking mechanism known to persons of ordinary skill in the art. The brake 122 is normally locked to maintain the preload of the payload (K1) member 110. However, the user can manually release the brake 122 to rotate the actuator 120 clockwise and reduce the payload (K1) member 110 preload. The brake mechanism 122 does not need to be limited to this particular architecture. Any of a number of brake designs could be used for the system 100 (e.g., a tripping mechanism or simple lock, as described in greater detail below). In some embodiments, the brake 122 can be adjusted in small increments to allow fine control of the payload (K1) member 110 preload. In other embodiments, however, the brake 122 may be adjustable in one or more single increments to allow the user, for example, to manipulate a high volume of the same payload having a known weight. The friction brake design shown is advantageous over a more common gear and pawl based design since it is not limited to discrete steps.

In some embodiments, the brake 122, as shown in FIGS. 11A,B, 12A,B and 13, may be based on a tripping mechanism. A tripping mechanism may preferably detect an imbalance, which may be a force-based or displacement-based (e.g., a pin from the payload arm 130 adapted to engage with another mechanism to lock a position—such as a ratcheting mechanism). In preferred embodiments, the tripping mechanism comprises a first and second handle (alternately referred to as the lifting arm 130 and the actuator 120 respectively). A user may move the first handle bi-directionally to either pick up or drop off a payload. The second handle is adapted to lag behind the first handle such that once a tripping condition is met, the second handle may jump forward and maintain the position of the first handle. In preferred embodiments, the first and second handles are connected on opposite sides of the system 100. In this way, the brake 122 may be more sensitive because as soon as the payload 10 begins to pick up, the tripping mechanism engages. Preferably, the user cannot overcome the brake 122 because once the payload 10 is lifted, the mechanism locks and cannot be overcome by the user. Persons skilled in the art will understand that many different tripping mechanisms known in the art may be used in the system 100. The tripping mechanism may be advantageous in systems 100 adapted to lift payloads 10 having unknown weights (or load vectors).

In other embodiments, the brake 122, as shown in FIGS. 11A,B, 12A,B and 13, may be based on a fixed position of the handle 120 (i.e., if the weight of the payload 10, or its load vector, is known). The system 100 may comprise a fixed brake 122 that will automatically stop the actuator 120 at a set, or predetermined, position (i.e., "on" or "off"). For example, if a payload of 50 lbs is picked up, a user can move the actuator 120 to a position corresponding to 50 lbs and then move the payload arm 130 to pick up the payload 10. This may be accomplished, for example, by a hook. This simple lock configuration, may be advantageous in situations where a user will be picking up the same payload 10 repeatedly as the complexity of the system 100 may be reduced by removing the tripping mechanism. Skilled readers will understand that systems 100 not having a tripping mechanism will still allow for the counterbalancing of payloads 10; however, the user will require a pre-determined position for the actuator 120 and configure the system 100 to maintain the actuator 120 in the pre-determined position.

In summary, the counterbalance system 100 contains two counterbalance assemblies 102,104. Each counterbalance contains two resilient members (i.e., 110 and 112 for the counterbalance arm assembly 102; 112 and 114 for the preload assembly 104). The payload (K1) member 110 is common to both assemblies 102,104 resulting in a total of three resilient members 110, 112, 114. The counterbalance arm assembly 102 counterbalances payloads 10 coupled to the lifting arm 130 by generating a lift vector. The preload assembly 104 is used to preload the payload (K1) member 110 of the counterbalance system 100. The actuator compensation (K3) member 114 is used to counterbalance the force experienced by the user as they rotate the preload assembly 104 to preload the payload (K1) member 110.

In a preferred embodiment, the system of the present invention may be applied in the design of a fully automated robotic arm for medical applications in which motors can be mounted onto the device to adjust the arm pose. Traditional designs may use high torque motors to counterbalance the arm and payload weight creating potential harm for the patient. In the event of a malfunction, these motors may potentially drive the arm into the patient with a minimum force of twice the weight of the arm. In the event of a power failure, a traditional arm may lose its pose and slump under its own weight as the motors can no longer counterbalance the weight. Brakes can be applied to prevent a traditional arm from slumping in a power failure. However, the traditional arm will become fully locked and its pose un-adjustable until power restored. In comparison, the system of the present invention is passively counterbalanced using resilient members. As a result, motors having low torque may be used to drive the system and motors are preferably not required to maintain a given pose. Furthermore, the system may be fully back-drivable allowing a given pose to be manually adjusted in the event of a power failure. The present system is unique amongst medical robotics since the arm provides an additional intrinsic level of safety over traditional medical robotic designs.

The system of the present invention preferably allows a user to quickly pick up a payload, having a known or unknown weight, with little or no effort. The system may be used with many different types of mechanical arms, including, for example, arms having industrial or medical uses.

Counterbalance systems, for example resilient member balance assemblies, described herein may be used in conjunction with further components as desired to aid in the orientation of mechanical arms, for example, without limitation, brakes for locking a hinged arm, encoders for measuring rotational angles of a hinged coupling, counterweights and/or other balances to offset the mass of the system, computer controlled actuators for automating actuation of a hinged coupling. Further components that may be incorporated into the mechanical arm will be apparent to the skilled person, and suitable combinations of optional components will also be apparent depending on the particular mechanical arm and the particular use of the mechanical arm.

As one example of an optional component, a counterweight may be mounted to the arm to offset the mass of a payload and/or mass of one or more elements of an articulated arm. Although the counterbalance mechanism described herein can eliminate the need for counterweights, counterweights may, if desired, be used in conjunction to offset the mass of the system.

As yet another example of an optional component, a braking mechanism may be mounted within the mechanical arm to inhibit or stop motion of arm elements relative to each other.

As still another example of an optional component, the mechanical arm may be equipped with motors (not shown), for example servo motors that may be controlled by a computer to automate the motion of various linkage elements. The counterbalance mechanism described herein reduces the force required by motors to actuate the mechanical arm.

As another example of an optional component, in embodiments where springs are used in a counterbalance assembly the compression or tension of one or more springs is adjustable.

Still further optional features will be apparent to the skilled person.

The present counterbalance system may be used in conjunction with many different types of mechanical arms, for example, arms having industrial or medical uses.

The system is preferably, but need not necessarily, capable of handling payloads weighing a few grams to about 100 kg and may depend on the length of the arms 120,130 and their respective ranges of motion.

Referring to FIGS. 4A and B, the counterbalance system 100 is preferably, but need not necessarily, symmetrical to allow the actuator 120 to lift a payload 10, while using the payload arm 130 to adjust for the payload weight.

The system is capable of handling multiple parts, and can serially pick up and drop off payloads, provided the process can be modeled as a closed system. Persons skilled in the art will understand that a closed system refers to no net gain or loss in the amount of energy stored within the three resilient members. While energy may be transferred between the resilient members, the total amount of energy between them remains constant. There must be no net energy gain or loss in handling the payload from pickup to drop off otherwise the arm must be equipped with an additional motor or resilient member to absorb the excess energy in the process. For example, an infinite conveyor of 100 lb weights coming in at one level ("L1") and the user is lifting a payload to a second elevational level ("L2"), there is a net energy input that you have to put in to go from L1 to L2. Once the payload is dropped off, you cannot pick up another payload at the same level, L2 without first picking up something of equal weight to that which was dropped off and bringing the arm down to L1. Another resilient member may be added to this three-resilient member counterbalance system for more energy capture to allow the mechanical arm to pick up and drop off payload in series. Energy is prestored in the resilient members allowing for one operation of the arm from L1 to L2. The motor operates via a feedback mechanism. It back-drives the energy back to the energy you want it to be at. At the point at which you drop off the payload, as soon as you squeeze the lever to release the load.

The present system allows the user to pick up and drop a payload at the same height. Dropping the load at a different height than picked up would result in the payload dropping or rising to the same height the load was originally picked up at. This is because there is either an excess or deficiency in the energy level of the resilient member loaded system as the resilient members were preloaded to match the energy level of the payload at pickup.

If it is desirable to release the payload at a different height than the pickup point, then it is necessary to change the energy level in the K1-K3, or second, assembly to match the height the payload is going to be dropped off at. To do this a motor (or resilient member and handle combo like the system used to preload the resilient member K1) is needed to rotate the cam assembly (A', e3, and e4 in FIG. 3) and the actuator compensation (K3) member, but payload (K1) member. Rotating this assembly clockwise will lower the safe drop off point of the load and a counterclockwise rotation will raise the drop off point of the payload.

If a resilient member-lever mechanism is used in place of a motor, once the user releases the load at an elevated height, for example, another load would have to be picked up at the drop off height and lowered before it is possible to raise a second payload. This limitation only applies to the resilient member-handle option and not the motor as the resilient member can only store a limited amount of energy and the motor has access to (in theory) an infinite amount of energy from the power grid.

The commercial applications of the apparatus are preferably wide ranging and span both the medical and non-medical fields. The apparatus may be valuable for any application where a user may encounter difficulties supporting or positioning a load (e.g., tool) or is required to quickly pick up a payload. Difficulties with respect to supporting or positioning the load may arise from: awkward motions, high load weight, maintaining a fixed position for long periods of time, are operating within confined spaces, or high positioning accuracy requirements. The apparatus of the present invention may be adapted to produce a lift vector to counterbalance the weight of any load (e.g., tool) engaged to the end of the lifting arm. In some embodiments, payloads, such as tools, on the end of the lifting arm can be translated and rotated as well as remain in position and/or orientation, if desired.

As an example, the system can be used to reduce many of the aggravating factors reported by individuals such as sonographers and vascular technologists. Loads, such as an ultrasound transducer, can be coupled onto the load bearing arm. The sonographer in this case, could manually adjust the position of the transducer until the desired imaging plane is acquired. The sonographer would then release the transducer and the apparatus should maintain the transducer position and apply the necessary transducer pressure. Use of the system would provide a solution related to prolonged arm abduction, prolonged twisting and application of transducer pressure by the sonographer.

Notably, the system can be scaled up for industrial applications (e.g., supporting heavy items) or down for entertainment applications (e.g., toy) as required. The foregoing are examples only and are not intended to limit the potential applications of the apparatus.

The embodiments of the present invention may also advantageously provide a simpler and more effective solution to counterbalance loads of known or unknown weight over the prior art. More specifically, the three resilient member counterbalance system may preferably be adapted for a mechanical arm, in which tools on the end of the arm can be translated and rotated by a human user and will remain in position once the user releases the arm. Furthermore, since the arm counterbalances the weight of the tool, the force the human user must exert to adjust the tool position is substantially reduced.

The figures present one potential implementation of the concept. Those skilled in the art would understand that the system of the present invention does not necessarily need to be a parallelogram structure and alternative architectures such as a simple lever can be used.

A novel counterbalance system that contains two counterbalance assemblies is provided. Each counterbalance contains two resilient members. One resilient member, the top resilient member, is common to both assemblies resulting in a total of three resilient members. The arm counterbalance assembly counterbalances the payload of the arm. A preload mechanism is used to preload the adjustable payload (K1) member of the arm counterbalance assembly. The second counterbalance assembly is used to counterbalance the force experienced by the user as they rotate the preload mechanism to preload the resilient member.

The foregoing description has been presented for the purpose of illustration and is not intended to be exhaustive or to limit the invention to the precise form disclosed. Other modifications, variations and alterations are possible in light of the above teaching and will be apparent to those skilled in the art, and may be used in the design and manufacture of other embodiments according to the present invention without departing form the spirit and scope of the invention. It is intended the scope of the invention be limited not by this description but only by the claims forming a part hereof.

The embodiments for which an exclusive privilege or property is claimed are as follows:

1. A counterbalance system for engaging a payload having a load vector in the direction of gravity, the system comprising:
   a payload (K1) member in communication with the payload to be engaged;
   a payload compensation (K2) member and an actuator compensation (K3) member in communication with either end of the payload (K1) member;
   an actuator, having a loaded and an unloaded position, in communication with the payload (K1) and the actuator compensation (K3) members, the payload (K1) and the actuator compensation (K3) members adapted to transfer an actuator energy during movement, of the actuator between the loaded and unloaded positions;

a payload arm adapted to support the payload, having a load-bearing and a neutral position, in communication with the payload (K1) and the payload compensation (K2) members, the payload (K1) and the payload compensation (K2) members adapted to transfer a support energy during movement of the payload arm between the load-bearing and neutral positions; and whereby, movement of the actuator to the loaded position when the payload arm is in the neutral position, transfers the actuator energy and the support energy to generate a lift vector at the payload to counterbalance the load vector.

2. The counterbalance system, according to claim 1, wherein the payload arm rotates about a first pivot and the actuator arm rotates about a second pivot.

3. The counterbalance system, according to claim 1, wherein the payload (K1) member, the payload compensation (K2) member and the actuator compensation (K3) member are adapted to exert an expansion force.

4. The counterbalance system, according to claim 1, wherein the payload (K1) member, the payload compensation (k2) member and the actuator compensation (K3) member are compression springs.

5. The counterbalance system, according to claim 2, further comprising first and second cams adapted to transfer the support energy between the payload (K1) member and the payload compensation (K2) member and third and fourth cams to transfer the actuator energy between the payload (K1) member and the actuator compensation (K3) member.

6. The counterbalance system, according to claim 5, wherein the first and second cams are mounted eccentrically in relation to the first pivot and the third and fourth cams are mounted eccentrically in relation to the second pivot.

7. The counterbalance system, according to claim 1, wherein the payload (K1) member, the payload compensation (K2) member and the actuator compensation (K3) member are adapted to exert a compression force.

8. The counterbalance system, according to claim 7, wherein the payload (K1) member, the payload compensation (K2) member and the actuator compensation (K3) member are extension springs.

9. The counterbalance system, according to claim 7, wherein the payload (K1) member and the payload compensation (K2) member are attached eccentrically in relation to one another to facilitate transfer of the support energy and the payload (K1) member and the actuator compensation (K3) member are attached eccentrically in relation to one another to facilitate transfer of the actuator energy.

10. The counterbalance system, according to claim 1, further comprising a brake adapted to maintain the actuator at a position.

11. The counterbalance system, according to claim 10, wherein the position corresponds with the load vector.

12. A method of engaging a payload having a load vector in the direction of gravity using a counterbalance system, the method comprising:

positioning a payload (K1) member in communication with the payload to be engaged;

positioning a payload compensation (K2) and an actuator compensation (K3) member in communication with either end of the payload (K1) member;

configuring an actuator, moveable between a loaded and an unloaded position, for communication with the payload (K1) and the actuator compensation (K3) members to transfer an actuator energy during movement of the actuator between the loaded and unloaded positions;

configuring a payload arm adapted to support the payload, moveable between a load-bearing and a neutral position, for communication with the payload (K1) and the actuator compensation (K2) members to transfer a support energy during movement of the payload arm between the load-bearing and neutral positions; and whereby, moving the actuator to the loaded position when the payload arm is in the neutral position, transfers the actuator energy and the support energy to generate a lift vector at the payload to counterbalance the load vector.

13. The method of claim 12, whereby the payload arm rotates about a first pivot and the actuator arm rotates about a second pivot.

14. The method of claim 12, whereby the payload (K1) member, the payload compensation (K2) member and the actuator compensation (K3) member are adapted to exert an expansion force.

15. The method of claim 2, further comprising first and second cams adapted to transfer the support energy between the payload (K1) member and the payload compensation (K2) member and third and fourth cams to transfer the actuator energy between the payload (k1) member and the actuator compensation (K3) member.

16. The method of claim 15, whereby the first and second cams are mounted eccentrically in relation to the first pivot and the third and fourth cams are mounted eccentrically in relation to the second pivot.

17. The method of claim 12, whereby the payload (K1) member, the payload compensation (K2) member and the actuator compensation (K3) member are adapted to exert a compression force.

18. The method of claim 17, whereby the payload (K1) member and the payload compensation (K2) member are attached eccentrically in relation to one another to facilitate transfer of the support energy and the payload (K1) member and the actuator compensation (K3) member are attached eccentrically in relation to one another to facilitate transfer of the actuator energy.

19. The method of claim 12, further comprising the step of maintaining the actuator at a position using a brake.

20. The method of claim 19, whereby the position of the brake corresponds to the load vector.

* * * * *